US 7,846,085 B2

(12) United States Patent
Silverman et al.

(10) Patent No.: US 7,846,085 B2
(45) Date of Patent: *Dec. 7, 2010

(54) KIT FOR FORMING IMPLANTS IN WALL OF GASTROINTESTINAL TRACT

(75) Inventors: David E. Silverman, Palo Alto, CA (US); Alan Stein, Moss Beach, CA (US); Edward J. Gough, San Carlos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 680 days.

This patent is subject to a terminal disclaimer.

(21) Appl. No.: 10/785,713

(22) Filed: Feb. 23, 2004

(65) Prior Publication Data

US 2004/0249239 A1    Dec. 9, 2004

Related U.S. Application Data

(63) Continuation of application No. 10/066,155, filed on Jan. 31, 2002, now Pat. No. 6,695,764, which is a continuation of application No. 09/538,863, filed on Mar. 29, 2000, now Pat. No. 6,358,197.

(60) Provisional application No. 60/148,838, filed on Aug. 13, 1999.

(51) Int. Cl.
*A61F 2/00* (2006.01)

(52) U.S. Cl. ....................................... 600/29

(58) Field of Classification Search .................. 600/29, 600/30, 350, 343, 361, 154; 606/193, 139, 606/144; 604/27, 48, 514, 890.1, 891.1; 128/903; 424/422, 423, 426, 450, 489; 525/937
See application file for complete search history.

(56) References Cited

U.S. PATENT DOCUMENTS 4,271,827 A    6/1981    Angelchik (Continued)

FOREIGN PATENT DOCUMENTS

AU    A-34223/95    5/1996

(Continued)

OTHER PUBLICATIONS

Aye, R.W. et al., "Early Results With the Laparoscopic Hill Repair", (May 1994), *Am. Jrnl. of Surgery*, vol. 167, pp. 542-546.
Collard, J.M. et al., "Laparoscopic Antireflux Surgery/What is Real Progress?", (1994), *Annals of Surgery*, vol. 220, No. 2, pp. 146-154.
DeMeester, T.R. et al., "Nissen Fundoplication for Gastroesophageal Reflux Disease", (1986), *Annals of Surgery*, vol. 204, No. 1, pp. 9-20.
Donahue, P. et al., "Endoscopic Sclerosis Of The Gastric Cardia For Prevention Of Experimental Gastroesophageal Reflux", (1990) *Gastrointestinal Endoscopy*, pp. 253-258.

(Continued)

*Primary Examiner*—Max Hindenburg
*Assistant Examiner*—Brian Szmal
(74) *Attorney, Agent, or Firm*—Mayer & Williams; David B. Bonham; Keum J. Park

(57) ABSTRACT

A kit for treating a gastrointestinal tract of a mammal and including a package and a tubular needle, an end piece and a container of an implant-forming material carried within the package. The end piece has an outer surface provided with at least one recess and an internal passageway communicating with the recess. The end piece is mounted on the distal extremity of an elongate probe member and introduced into the upper portion of the gastrointestinal tract. A portion of the wall of the gastrointestinal tract is drawn into the recess and the tubular needle is extended through the elongate probe member and the internal passageway into the portion of the wall in the recess. Material from the container is loaded into the tubular needle and injected into the portion of the wall to form an implant in the wall.

28 Claims, 9 Drawing Sheets

U.S. PATENT DOCUMENTS

| | | | |
|---|---|---|---|
| 4,424,208 A | 1/1984 | Wallace et al. | |
| 4,582,640 A | 4/1986 | Smestad et al. | |
| 4,763,667 A | 8/1988 | Manzo | |
| 4,773,393 A | 9/1988 | Haber et al. | |
| 4,803,075 A | 2/1989 | Wallace et al. | |
| 4,837,285 A | 6/1989 | Berg et al. | |
| 5,007,940 A | 4/1991 | Berg | |
| 5,067,965 A | 11/1991 | Ersek et al. | |
| 5,116,387 A | 5/1992 | Berg | |
| 5,158,573 A | 10/1992 | Berg | |
| 5,204,382 A | 4/1993 | Wallace et al. | |
| 5,258,028 A | 11/1993 | Ersek et al. | |
| 5,314,473 A | 5/1994 | Godin | |
| 5,336,263 A | 8/1994 | Ersek et al. | |
| 5,451,406 A | 9/1995 | Lawin et al. | |
| 5,480,644 A | 1/1996 | Freed | |
| 5,490,984 A | 2/1996 | Freed | |
| 5,580,568 A | 12/1996 | Greff et al. | |
| 5,584,861 A | 12/1996 | Swain et al. | |
| 5,667,767 A | 9/1997 | Greff et al. | |
| 5,695,480 A | 12/1997 | Evans et al. | |
| 5,744,153 A * | 4/1998 | Yewey et al. | 424/426 |
| 5,755,658 A | 5/1998 | Wallace et al. | |
| 5,755,730 A | 5/1998 | Swain et al. | |
| 5,785,642 A | 7/1998 | Wallace et al. | |
| 5,792,153 A | 8/1998 | Swain et al. | |
| 5,792,478 A | 8/1998 | Lawin et al. | |
| 5,830,178 A | 11/1998 | Jones et al. | |
| 5,855,615 A | 1/1999 | Bley et al. | |
| 5,861,036 A | 1/1999 | Godin | |
| 6,010,515 A | 1/2000 | Swain et al. | |
| 6,059,719 A | 5/2000 | Yamamoto et al. | |
| 6,098,629 A | 8/2000 | Johnson et al. | |
| 6,210,378 B1 * | 4/2001 | Ouchi | 600/154 |
| 6,251,063 B1 * | 6/2001 | Silverman et al. | 600/29 |
| 6,285,897 B1 * | 9/2001 | Kilcoyne et al. | 600/350 |
| 6,335,028 B1 | 1/2002 | Vogel et al. | |
| 6,338,345 B1 | 1/2002 | Johnson et al. | |
| 6,358,197 B1 | 3/2002 | Silverman et al. | |
| 6,368,334 B1 * | 4/2002 | Sauer | 606/139 |
| 6,379,373 B1 * | 4/2002 | Sawhney et al. | 606/193 |

FOREIGN PATENT DOCUMENTS

| | | |
|---|---|---|
| EP | 0 711 548 A | 5/1996 |
| JP | 5-64642 A | 3/1993 |
| WO | WO 93/19702 A | 10/1993 |
| WO | WO 95/25468 A | 9/1995 |
| WO | WO 97/19643 | 6/1997 |
| WO | WO 97/45131 | 12/1997 |
| WO | WO 98/01088 | 1/1998 |
| WO | WO 98/17200 | 4/1998 |
| WO | WO 98/17201 | 4/1998 |
| WO | WO 99/13785 A1 | 3/1999 |

OTHER PUBLICATIONS

Donahue, P.E. et al., "The Floppy Nissen Fundoplication/ Effective Long-term Control of Pathologic Reflux", (Jun. 1985), *Arch Surg*, vol. 120, pp. 663-668.
Ellis, Jr., F.H., "The Nissen Fundoplication", (1992), *Ann. Thorac. Surg.*, vol. 54, pp. 1231-1235.
Grande, L. et al., "Value of Nissen fundoplication in patients with gastro-oesophageal reflux judged by long-term sympton control", (1994), *Brit. Jnl. of Surgery*, vol. 81, pp. 548-550.
Hill, L.D. et al., "Laparoscopic Hill Repair", (Jan. 1994), *Contemporary Surgery*, vol. 44, No. 1, pp. 13-20.
Hunter, J.G. et al., "A Physiologic Approach to Laparoscopic Fundoplication for Gastroesophageal Reflux Disease", (1996), *Annals of Surgery*, vol. 223, No. 6, pp. 673-687.
Ireland, A.C. et al., "Mechanisms underlying the antireflux action of fundoplication", (1993), *Gut*, vol. 34, pp. 303-308.
Johansson, J. et al., "Outcome 5 years after 360° fundoplication for gastro-oesophageal reflux disease", (Jan. 1993), *Brit. Jnl. of Surgery*, vol. 80, pp. 46-49.
Kauer, W.K.H. et al., "Mixed Reflux of Gastric and Duodenal Juices Is More Harmful to the Esophagus than Gastric Juice Alone/The Need for Surgical Therapy Re-Emphasized", (1995) *Annals of Surgery*, vol. 222, No. 4, pp. 525-533.
Klingman, R.R. et al., "The Current Management of Gastroesophageal Reflux", (1991), *Adv. Surg.*, vol. 24, pp. 259-291.
Little, A.G., "Mechanisms of Action of Antireflux Surgery: Theory and Fact", (1992), *World Jnl. of Surgery*, vol. 16, pp. 320-325.
Luostarinen, M., "Nissen Fundoplication for Reflux Esophagitis/ Long-Term Clinical and Endoscopic Results in 109 of 127 Consecutive Patients", (1993), *Annals of Surgery*, vol. 217, No. 4, pp. 329-337.
Luostarinen, M. et al., "Fate of Nissen fundoplication after 20 years. A clinical, endoscopical, and functional analysis", (1993), *Gut*, vol. 34, pp. 1015-1020.
Malizia, A. et al., "Migration and Granulomatous Reaction After Periurethral injection of Polytef (Teflon)", (Jun. 1984), *JAMA*, vol. 251, No. 24, pp. 3277-3281.
Martin, C. et al., "Collis-Nissen Gastroplasty Fundoplication For Complicated Gastro-Oesophageal Reflux Disease", (1992), *Aust. N.Z. Jnl. Surg.*, vol. 62, pp. 126-129.
O'Connor, K.W. et al., "Endoscopic placement of collagen at the lower esophageal sphincter to inhibit gastroesophageal reflux: a pilot study of 10 medically intractable patients", (1988), *Gastrointestinal Endoscopy*, vol. 34, No. 2, pp. 106-112.
O'Connor, K.W. et al., "An experimental endoscopic technique for reversing gastroesophageal reflux in dogs by injecting inert material in the distal esophagus", (1984), *Gastrointestinal Endoscopy*, vol. 30, No. 5, pp. 275-280.
Ortiz, A. et al., "Conservative treatment versus antireflux surgery in Barrett's oesophagus: long-term results of a prospective study", (1996), *Brit. Jnl. of Surg.*, vol. 83, 274-278.
Politano, V. et al., "Periurethral Teflon Injection for Urinary Incontinence", ( Feb. 1974) *Jnl. Urology*, vol. 111, pp. 180-183.
Pope, C., "The Quality of Life Following Antireflux Surgery", (1992), *World Jnl. of Surgery*, vol. 16, pp. 355-358.
Schulman, C.C. et al., "Endoscopic injections of Teflon to treat urinary incontinence in women", (Jan. 21, 1984) *BMJ*, vol. 228, p. 192.
Shafik, A., "Intraesophageal Polytef injection for the treatment of reflux esophagitis", (1996), *Surgical Endoscopy*, pp. 329-331.
Shirazi, S.S. et al., "Long-term Follow-up for Treatment of Complicated Chronic Reflux Esophagitis", (May 1987), *Arch Surg*, vol. 122, 548-552.
Society of Am. Gastrointestinal Endoscopic Surgeons, Los Angeles, CA, "Granting of Privileges for Laparascopic General Surgery", (Mar. 1991), *Am. Jrnl. of Surgery*, vol. 161, pp. 324-325.
Spechler, S.J. et al., "Comparison of Medical and Surgicl Therapy for Complicated Gastroesophageal Reflux Disease in Veterans", (Mar. 19, 1992), *NE Jnl. of Med*, vol. 326, No. 12, pp. 786-792.
Spechler, S.J. et al., "The Columnar-Lined Esophagus, Intestinal Metaplasia, and Norman Barrett", (1996), *Gastroenterology*, vol. 110, pp. 614-621.
Thor, K.B. et al., "A Long-Term Randomized Prospective Trial of the Nissen Procedure Versus a Modified Toupet Technique", (Dec. 1989), *Ann. Surg.*, vol. 210, No. 6, pp. 719-724.
Vaezi, M.F. et al., "Synergism of acid and duodenogastroesophageal reflux in complicated Barrett's esophagus", (1995), *Surgery*, vol. 117, pp. 699-704.
Walker, R.D. et al., "Injectable Bioglass as a Potential Substitute for Injectable Polytetrafluoroethylene", (Aug. 1992),*J. Urol.*, vol. 148, pp. 645-647.
Waring, J.P. et al., "The Preoperative Evaluation of Patients Considered for Laparoscopic Antireflux Surgery", (1995), *Am. Jnl. Of Gastroenterology*, vol. 90, No. 1, pp. 35-38.

* cited by examiner

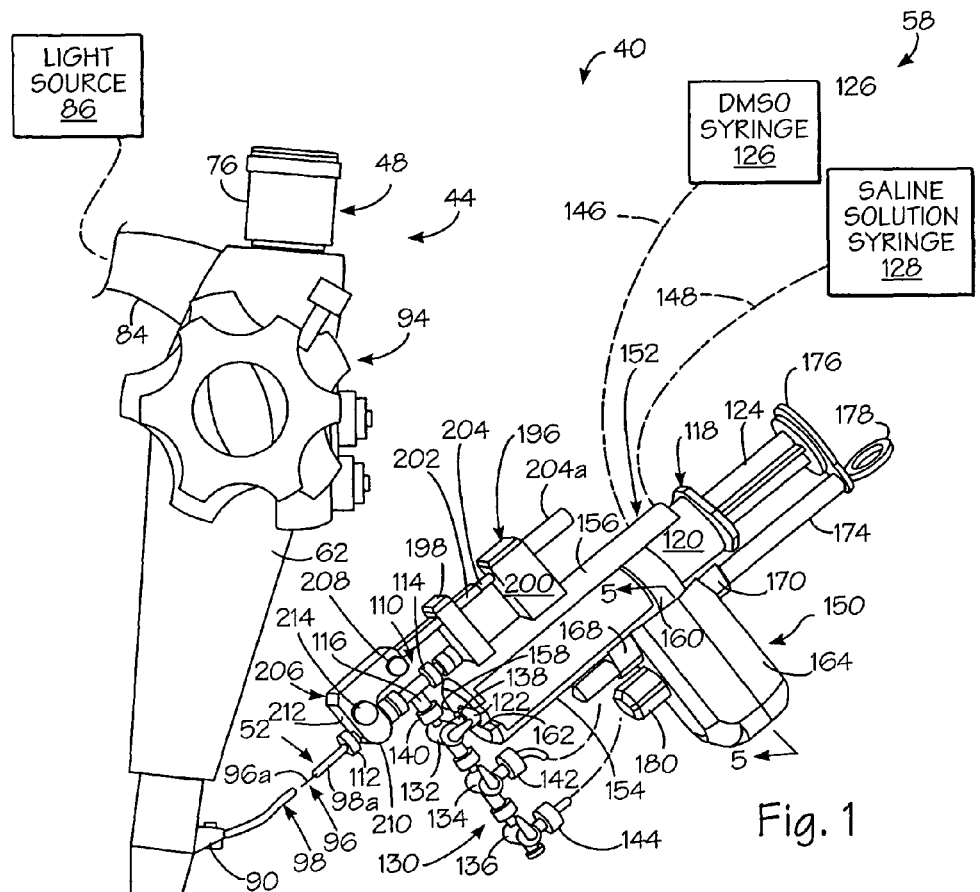
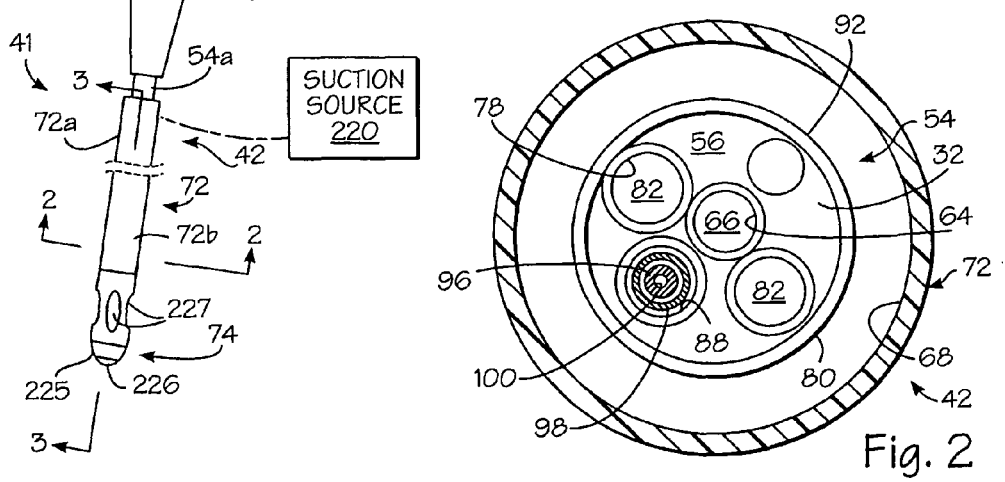

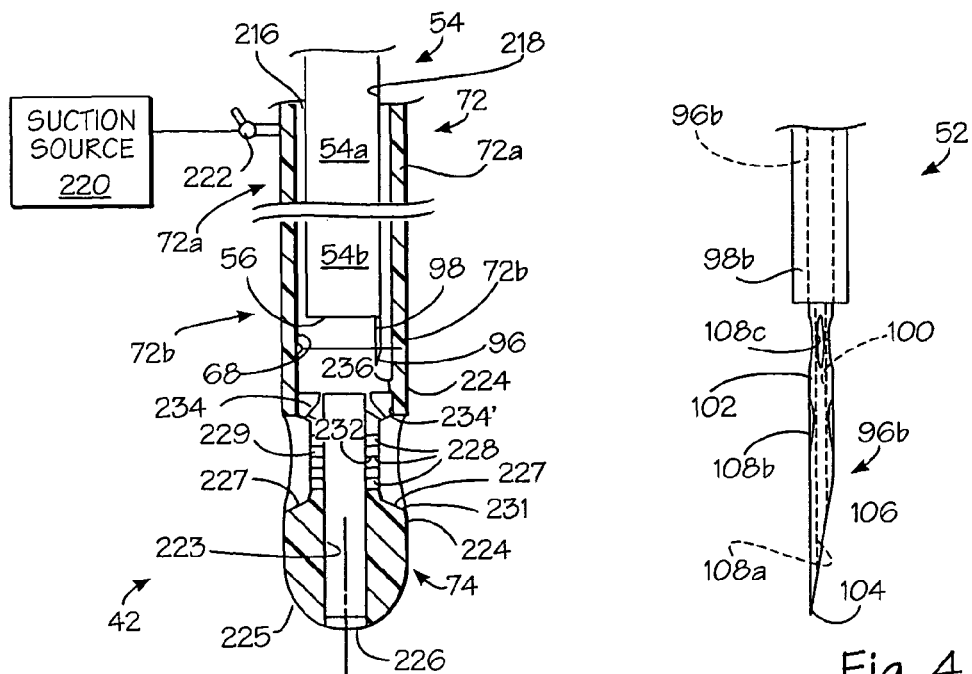
Fig. 3
Fig. 4
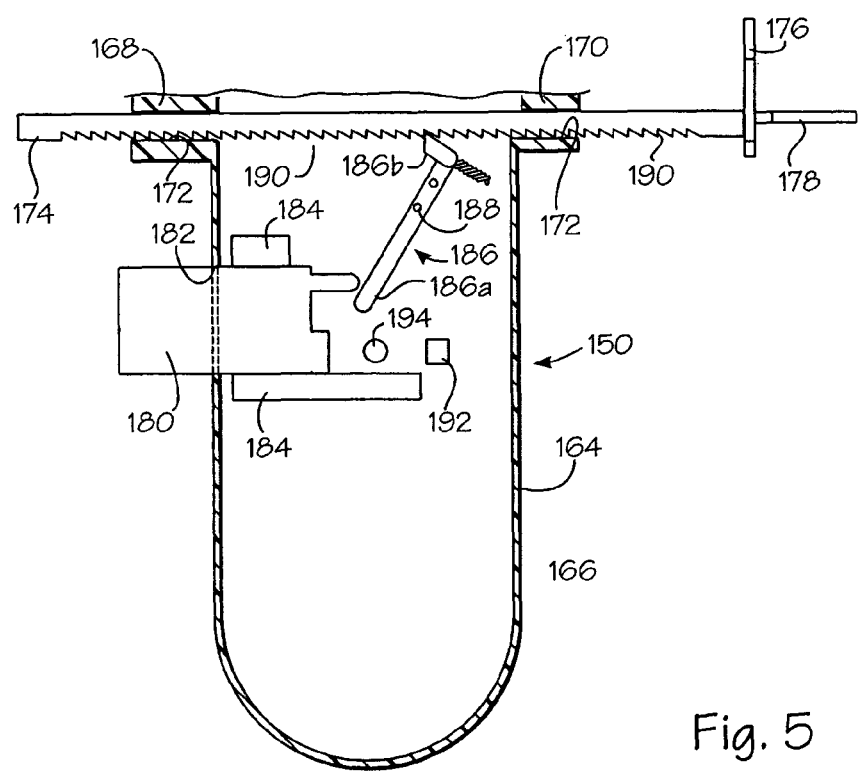
Fig. 5

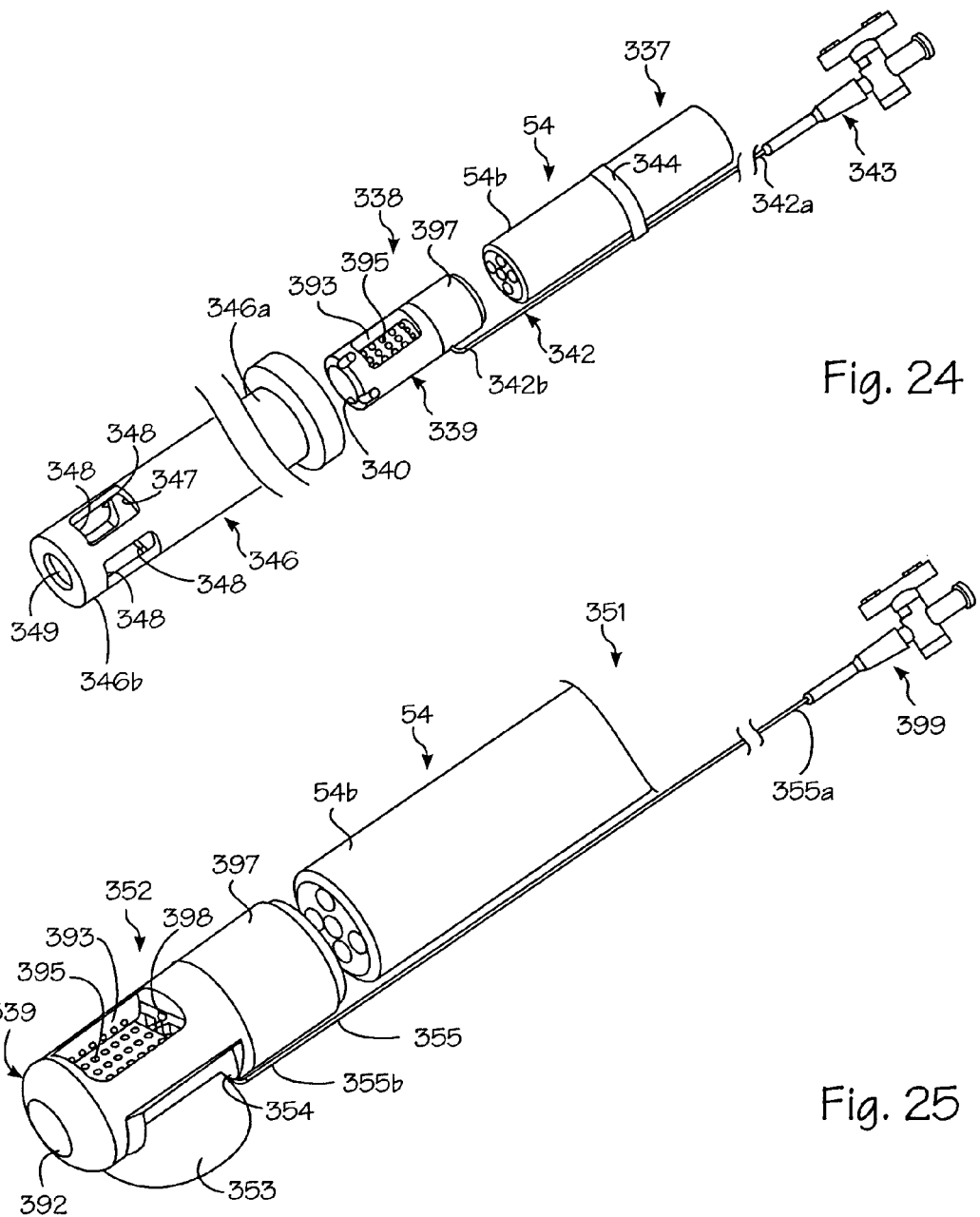

KIT FOR FORMING IMPLANTS IN WALL OF GASTROINTESTINAL TRACT

CROSS-REFERENCE TO RELATED APPLICATIONS

This application is a continuation of U.S. patent application Ser. No. 10/066,155 filed Jan. 31, 2002, now U.S. Pat. No. 6,695,764, which is a continuation of U.S. patent application Ser. No. 09/538,863 filed Mar. 29, 2000, now U.S. Pat. No. 6,358,197, which claims priority to U.S. provisional patent application Ser. No. 60/148,838 filed Aug. 13, 1999, the entire content of each of which is incorporated herein by this reference.

BACKGROUND OF THE INVENTION

1. Field of the Invention

This invention pertains to the treatment of a portion of a wall forming a cavity in a body. More particularly, this invention pertains to an apparatus for forming implants in a portion of the wall forming the gastrointestinal tract.

2. Description of Related Art

Gastroesophageal reflux disease (GERD) is a failure of the anti-reflux barrier, allowing abnormal reflux of gastric contents into the esophagus of the gastrointestinal tract. Gastroesophageal reflux disease is a disorder which is usually characterized by a defective lower esophageal sphincter (LES), a gastric emptying disorder with or without failed esophageal peristalsis. The disease usually manifests itself during "transient lower esophageal sphincter relaxation" episodes, the frequency of which is greatly increased in patients who reflux. Medical or drug therapy is the first line of management for gastroesophageal refluxes. However, drug management does not address the condition's mechanical etiology. Thus symptoms recur in a significant number of sufferers within one year of drug withdrawal. In addition, while medical therapy may effectively treat the acid-induced symptoms of gastroesophageal reflux disease, esophageal mucosal injury may continue due to ongoing alkaline reflux. Since gastroesophageal reflux disease is a chronic condition, medical therapy involving acid suppression and/or promotility agents may be required for the rest of a patient's life.

The expense and psychological burden of a lifetime of medication dependence, undesirable life style changes, uncertainty as to the long term effects of some newer medications and the potential for persistent mucosal changes despite symptomatic control, all make surgical treatment of gastroesophageal reflux disease an attractive option. Unfortunately, surgical intervention is a major operation with all attendant morbidities, mortality and risk of failure requiring further surgery in the case of over-correction. Laparoscopic surgery requires a very high level of skill and special training for it to be successful.

Minimally invasive procedures have been provided for forming implants in the wall of the gastrointestinal tract to treat GERD and other ailments. It would be desirable to have a method and device for forming implants of a predetermined size in a consistent manner to enhance the reproducibility of such procedures.

OBJECTS AND SUMMARY OF THE INVENTION

In general, it is an object of the present invention to provide a minimally invasive apparatus for injecting a material into a portion of a wall forming a cavity in a body, such as the gastrointestinal tract, to form one or more implants of a substantially consistent size in the wall.

Another object of the invention is to provide an apparatus of the above character in which a recess in a probe is utilized to shape the portion of the wall into a protrusion into which the material is injected.

Another object of the present invention is to provide an apparatus of the above character in which the probe guides and positions an injection needle into the protrusion.

Another object of the present invention is to provide an apparatus of the above character in which consistently sized multiple implants may be formed in a portion of the wall of the cavity.

Another object of the present invention is to provide an apparatus of the above character which can inhibit the injection need from being pushed through the wall.

Another object of the present invention is to provide an apparatus of the above character which can be used for treating gastroesophageal reflux disease (GERD).

In general, an apparatus comprising an elongate probe member having proximal and distal extremities has been provided for use with a suction source to treat a portion of a wall forming a cavity in a body having a natural body opening for accessing the cavity. The elongate probe member has a length so that when the distal extremity is in the vicinity of the portion of the wall the proximal extremity is outside of the body. The distal extremity of the elongate probe member has an outer surface and is provided with at least one recess opening onto the outer surface and an internal passageway communicating with the recess. When the suction source is coupled to the apparatus a suction is created in the recess by means of the passageway to draw the portion of the wall into the recess. A hollow needle is slidably disposed in the elongate probe member and has a distal end portion. The needle is actuatable from outside the body for movement from a retracted position in which the distal end portion of the needle is out of the recess and an extended position in which the distal end portion of the needle extends into the recess. The needle can be extended into the portion of the wall drawn into the recess so as to introduce a material into the portion of the wall and form an implant in the portion of the wall.

BRIEF DESCRIPTION OF THE DRAWINGS

FIG. 1 is a perspective view of an apparatus for treating a portion of a wall forming a cavity in a body in accordance with the present invention.

FIG. 2 is a cross-sectional view of the apparatus of FIG. 1 taken along line 2-2 of FIG. 1.

FIG. 3 is a cross-sectional view of a portion of the apparatus of FIG. 1 taken along line 3-3 of FIG. 1.

FIG. 4 is an enlarged side view of a portion of the apparatus of FIG. 3.

FIG. 5 is a cross-sectional view of a proximal portion of the apparatus of FIG. 1 taken along the line 5-5 of FIG. 1.

FIG. 24 is a perspective view of a distal portion of yet a further embodiment of the apparatus of the present invention.

FIG. 25 is a perspective view of a distal portion of another embodiment of the apparatus of the present invention.

DESCRIPTION OF THE PREFERRED EMBODIMENTS

Figure 6:
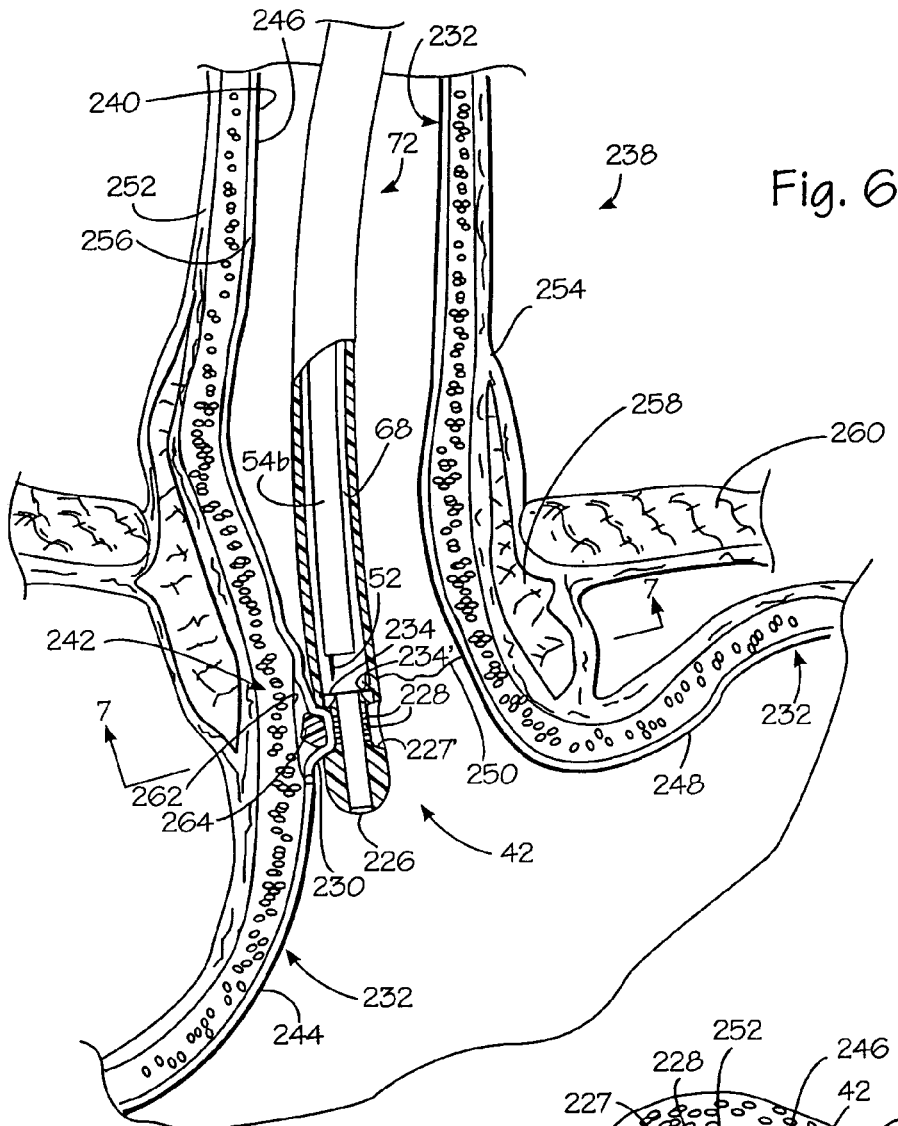
FIG. 6 is an elevational view of the apparatus of FIG. 1 treating a lower esophageal sphincter in accordance with the present invention.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

In general, an apparatus 40 for treating the gastrointestinal tract in a body of a mammal is provided. The apparatus 40 comprises an elongate probe member 41 that can include an overtube member and/or overtip member used in combination with a probe for introducing a material into a wall of the gastrointestinal tract to form one or more implants in the wall. In one embodiment shown in FIG. 1, a tubular assembly such as an overtube assembly 42 is used in combination with a conventional probe device 44 to form a protrusion in a portion of the wall of the gastrointestinal tract into which an implant-forming solution is injected. Medical apparatus or medical treatment device 40 shown in FIG. 1 includes probe member or probe 44 and overtube assembly 42, with the overtube assembly 42 being considered part of the distal extremity of elongate probe member 41. An optical viewing device 48 is included in probe 44 and a needle assembly 52 is slidably carried by elongate probe member 41, and in this embodiment by probe 44. Treatment device 40 further includes a supply assembly 58 mounted to the proximal end portion of needle assembly 52. Overtube assembly 42 is removably mounted on the distal extremity of probe 44. In another embodiment, a shortened tubular assembly such as an overtip assembly is used in combination with the probe, instead of an overtube assembly, to form a protrusion and introduce the solution. In a further embodiment, an overtube member is used in combination with an overtip assembly and a probe. In each embodiment, a solid is formed in the wall from the material to treat the wall. A kit for use in the above procedure is provided.

A conventional or other suitable gastroscope or endoscope can be used for probe 44. The exemplary probe 44 shown in FIGS. 1-3 is an Olympus CF Type 40L/I endoscope made by Olympus Corporation of Tokyo Japan. Probe 44 includes a flexible elongate tubular member or insertion tube 54 having proximal and distal extremities 54a and 54b and a distal face 56. A handle means or assembly is coupled to proximal extremity 54a of elongate first member or insertion tube 54 and includes a conventional probe handle 62. The tubular insertion tube 54 includes a plurality of bores or passageways extending axially from proximal extremity 54a to distal extremity 54b. A plurality of five such passageways, including a central passageway 64, are shown in FIG. 2.

Referring to FIGS. 1 and 2, optical viewing device 48 is formed integral with probe 44 and has an optical element or objective lens 66 carried by the central passageway 64 of insertion tube 54. Lens 66 has a field of view at distal face 56 which permits the operator to view forwardly of insertion tube distal extremity 54b. In particular, lens 66 has a field of view that includes the portion of a pressure chamber 68 formed within a distal end 72b of a second member or overtube member 72 and the portion of end cap 74 which are located forwardly of insertion tube distal extremity. Optical viewing device 48 further includes an eye piece 76 mounted on a proximal end of probe handle 62. Second and third illumination passageways 78, 80 are provided in insertion tube 54 peripherally of central passageway 64 for carrying respective light fiber assemblies or light guides 82. A connection cable 84, a portion of which is shown in FIG. 1, extends from probe handle 62 to a conventional light source 86. First and second light guides 82 extend through insertion tube 54 and cable 84 for providing illumination forwardly of insertion tube 54.

A working passageway or channel 88 is further provided in insertion tube 54 and extends to a side port 90 formed in probe handle 62. An additional passageway 92 extends through insertion tube 54 and can be used as an air and/or water inlet or outlet or a lumen for providing suction. Insertion tube 54 is flexible so as to facilitate its insertion and advancement through a body and includes a bendable distal end for selectively directing distal face 56 in a desired direction. A plurality of finger operable controls 94 are provided on probe handle 62 for, among other things, operating the bendable distal end of insertion tube 54 and the supply and removal of fluids through the insertion tube 54.

Referring to FIGS. 1 and 4, needle assembly 52 can be of any conventional type such as a modified sclerotherapy needle similar to the Bard® Flexitip™ needle manufactured by C.R. Bard, Inc. of Billerica, Md. Needle assembly 52 includes a needle member or needle 96 having a proximal end portion 96a and a distal end portion 96b. Needle assembly 52 may include an optional sleeve member or sleeve 98 having a proximal end portion or extremity 98a and a distal end portion or extremity 98b. Sleeve or elongate tubular member 98 is made from any suitable material such as flexible plastic or metal and has a lumen extending longitudinally therethrough for receiving needle 96. The sleeve 98 and the needle 96 are slidable relative to each other in a longitudinal direction. In this regard, tubular needle 96 is slidably disposed in sleeve 98 and movable from a retracted position in which tubular needle 96 is recessed within distal end portion 98b to an extended position in which needle 96 projects distally of sleeve 98. Needle 96 and sleeve 98 can be slidably disposed within working channel 88 and side port 90 of insertion tube 54 and each have a length so that when distal end portions 96b and 98b are extending from distal extremity 54b of insertion tube 54 or otherwise in the vicinity of distal face 56, proximal end portions 96a and 98a are accessible at side port 90. Needle 96 is provided with a lumen or internal passage 100 extending longitudinally therethrough for carrying liquids or other materials through the needle.

Hollow or tubular needle 96 has an internal passage 100 extending longitudinally therethrough from proximal end portion 96a to distal end portion 96b. The modified needle distal end portion 96b is made from any suitable material such as stainless steel and has a size ranging from 16 to 28 gauge and preferably ranging from 21 to 26 gauge. As shown most clearly in FIG. 4, the distal end portion 96b has a cylindrical wall 102 for forming internal passage 100 and also has a sharpened or beveled distal end 104 formed in part by a tapered end surface 106. At least one opening is provided in distal end portion 96b and can include or consist of an opening 108a provided in tapered end surface 106. As an alternative to or in addition to opening 108a, at least one and as shown a plurality of openings can be provided in cylindrical wall 102. For example, two openings 108b and two additional openings 108c are provided in wall 102. Openings 108b are diametrically disposed relative to each other, so as to be 180° apart, and openings 108c are also diametrically disposed relative to each other but offset 90° from openings 108b. The openings 108c are spaced longitudinally behind the openings 108b. Openings 108b and 108c can be any suitable shape or size and are shown as being elongate or oblong in shape.

It should be appreciated that a needle distal end portion 96b having only openings 108b or openings 108c can be provided and be within the scope of the present invention. In one embodiment (not shown), tapered surface 106 may be closed and openings 108 are provided only in cylindrical wall 102. Needle proximal end portion 96a and the central portion of needle 96 can be made from plastic, metal or any other suitable material. Other needle configurations may also be used. For example, the needle may be provided with a sharpened or pointed distal end which is generally conical in shape and has no opening (not shown). Also, three or more circumferentially-disposed openings may be provided at substantially equal separation angles. For example, in the case of three circumferentially spaced openings, each may be spaced 120° from the other openings (not shown).

A fluid connector 110 is secured or coupled to proximal end portion 96a of needle 96 and a gripping member or grip 112 is secured to the proximal end portion 98a of sleeve 98, as shown in FIG. 1. Fluid connector 110 includes first and second Luer fitting portions 114 and 116, or any other suitable fitting portions, which communicate with passage 100 in needle 96. First Luer fitting portion 114 is capped in FIG. 1. Fluid connector 110 and grip 112 are longitudinally movable relative to each other so as to cause relative longitudinal movement between needle 96 and sleeve 98. More specifically, grip 112 can be slid forwardly and rearwardly on proximal end portion 96a of needle 96 relative to fluid connector 110. Movement of grip 112 forwardly relative to fluid connector 110 causes distal end portion 98b of sleeve 98 to extend fully over distal end portion 96b of needle 96 so that the needle has fully retracted within sleeve 98. Conversely, movement of grip 112 rearwardly relative to fluid connector 110 causes sleeve distal end portion 98b to retract relative to needle distal end portion 96b so as to expose needle distal end portion 96b.

The handle means of treatment device 40 includes supply assembly 58 coupled to proximal extremity 54a of insertion tube 54 (FIG. 1). More specifically, supply assembly 58 is secured to the proximal extremity of needle assembly 52. The supply assembly 58 is included within the means of treatment device 40 for introducing a liquid, solution or other material through passage 100 of needle 96 and out one or more of the openings 108 provided in needle distal end portion 96b. Supply assembly 58 may comprise a conventional syringe or first syringe 118 having a reservoir or barrel 120 provided with any suitable fitting portion such as Luer fitting portion 122 at the forward end thereof and a plunger 124 for dispelling liquid within barrel 120 through Luer fitting portion 122.

Any suitable material, from which an implant can be formed when the fluid, separately or in conjunction with another fluid, is introduced into the body, can be provided in syringe 118. Although aqueous or non-aqueous solutions are amongst the fluids that can be used, an inert, nonresorbable material is preferred. One such material comprises at least one solution which when introduced into the body forms a nonbiodegradable solid. As used herein, a solid means any substance that does not flow perceptibly under moderate stress, has a definite capacity for resisting forces which tend to deform it (such as compression, tension and strain) and under ordinary conditions retains a definite size and shape; such a solid includes, without limitation, spongy and/or porous substances. One such embodiment of the at least one solution is first and second solutions which when combined in the body form the nonbiodegradable solid. Another such embodiment is a nonaqueous solution which can be introduced into the body as a liquid and from which a solid thereafter precipitates. A preferred embodiment of such a nonaqueous solution is a solution of a biocompatible polymer and a biocompatible solvent which can optionally include a contrast agent for facilitating visualization of the solution in the body.

A particularly preferred implant-forming or bulking solution is a composition comprising from about 2.5 to about 8.0 weight percent of a biocompatible polymer, from about 52 to about 87.5 weight percent of a biocompatible solvent and optionally from about 10 to about 40 weight percent of a biocompatible contrast agent having a preferred average particle size of about 10 µm or less. It should be appreciated that any percentages stated herein which include a contrast agent would be proportionally adjusted when the contrast agent is not utilized. Any contrast agent is preferably a water insoluble biocompatible contrast agent. The weight percent of the polymer, contrast agent and biocompatible solvent is based on the total weight of the complete composition. In a preferred embodiment, the water insoluble, biocompatible contrast agent is selected from the group consisting of barium sulfate, tantalum powder and tantalum oxide. In still a further preferred embodiment, the biocompatible solvent is dimethylsulfoxide (DMSO), ethanol, ethyl lactate or acetone.

The term "biocompatible polymer" refers to polymers which, in the amounts employed, are non-toxic, chemically inert, and substantially non-immunogenic when used internally in the patient and which are substantially insoluble in physiologic liquids. Suitable biocompatible polymers include, by way of example, cellulose acetates (including cellulose diacetate), ethylene vinyl alcohol copolymers, hydrogels (e.g., acrylics), poly($C_1$-$C_6$) acrylates, acrylate copolymers, polyalkyl alkacrylates wherein the alkyl and alk groups independently contain one to six carbon atoms, polyacrylonitrile, polyvinylacetate, cellulose acetate butyrate, nitrocellulose, copolymers of urethane/carbonate, copolymers of styrene/maleic acid, and mixtures thereof. Copolymers of urethane/carbonate include polycarbonates that are diol terminated which are then reacted with a diisocyanate such as methylene bisphenyl diisocyanate to provide for the urethane/carbonate copolymers. Likewise, copolymers of styrene/maleic acid refer to copolymers having a ratio of styrene to maleic acid of from about 7:3 to about 3:7. Preferably, the biocompatible polymer is also non-inflammatory when employed in situ. The particular biocompatible polymer employed is not critical and is selected relative to the viscosity of the resulting polymer solution, the solubility of the biocompatible polymer in the biocompatible solvent, and the like. Such factors are well within the skill of the art.

The polymers of polyacrylonitrile, polyvinylacetate, poly ($C_1$-$C_6$) acrylates, acrylate copolymers, polyalkyl alkacrylates wherein the alkyl and alk groups independently contain one to six carbon atoms, cellulose acetate butyrate, nitrocellulose, copolymers of urethane/carbonate, copolymers of styrene/maleic acid and mixtures thereof typically will have a molecular weight of at least about 50,000 and more preferably from about 75,000 to about 300,000.

Preferred biocompatible polymers include cellulose diacetate and ethylene vinyl alcohol copolymer. In one embodiment, the cellulose diacetate has an acetyl content of from about 31 to about 40 weight percent. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the implanting properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 8 weight-volume percent of the ethylene vinyl alcohol copolymer in DMSO has a viscosity equal to or less than 60 centipoise at 20° C. and more preferably 40 centipoise or less at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution. In a particularly preferred embodiment, the copolymers employed herein comprise a mole percent of ethylene of from about 25 to about 60 and a mole percent of vinyl alcohol of from about 40 to about 75, more preferably a mole percent of ethylene of from about 40 to about 60 and a mole percent of vinyl alcohol of from about 40 to about 60.

The term "contrast agent" refers to a biocompatible (non-toxic) radiopaque material capable of being monitored during injection into a mammalian subject by, for example, radiography. The contrast agent can be either water soluble or water insoluble. Examples of water soluble contrast agents include metrizamide, iopamidol, iothalamate sodium, iodomide sodium, and meglumine. The term "water insoluble contrast agent" refers to contrast agents which are insoluble in water (i.e., has a water solubility of less than 0.01 milligrams per milliliter at 20° C.) and include tantalum, tantalum oxide and barium sulfate, each of which is commercially available in the proper form for in vivo use and preferably having a particle size of 10 µm or less. Other water insoluble contrast agents include gold, tungsten and platinum powders. Methods for preparing such water insoluble biocompatible contrast agents having an average particle size of about 10 µm or less are described below. Preferably, the contrast agent is water insoluble (i.e., has a water solubility of less than 0.01 mg/ml at 20° C.)

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, ethyl lactate, acetone, and the like. Aqueous mixtures with the biocompatible solvent can also be employed provided that the amount of water employed is sufficiently small that the dissolved polymer precipitates upon injection into a human body. Preferably, the biocompatible solvent is ethyl lactate or dimethylsulfoxide.

The term "encapsulation" as used relative to the contrast agent being encapsulated in the precipitate is not meant to infer any physical entrapment of the contrast agent within the precipitate much as a capsule encapsulates a medicament. Rather, this term is used to mean that an integral coherent precipitate forms which does not separate into individual components, for example into a copolymer component and a contrast agent component.

The compositions employed in the methods of this invention are prepared by conventional methods whereby each of the components is added and the resulting composition mixed together until the overall composition is substantially homogeneous. For example, sufficient amounts of the selected polymer are added to the biocompatible solvent to achieve the effective concentration for the complete composition. Preferably, the composition will comprise from about 2.5 to about 8.0 weight percent of the polymer based on the total weight of the composition and more preferably from about 4 to about 5.2 weight percent. If necessary, gentle heating and stirring can be used to effect dissolution of the polymer into the biocompatible solvent, e.g., 12 hours at 50° C.

Sufficient amounts of the contrast agent are then optionally added to the biocompatible solvent to achieve the effective concentration for the complete composition. Preferably, the composition will comprise from about 10 to about 40 weight percent of the contrast agent and more preferably from about 20 to about 40 weight percent and even more preferably about 30 to about 35 weight percent. When the contrast agent is not soluble in the biocompatible solvent, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Each of the polymers recited herein is commercially available but can also be prepared by methods well known in the art. For example, polymers are typically prepared by conventional techniques such as radical, thermal, UV, gamma irradiation, or electron beam induced polymerization employing, as necessary, a polymerization catalyst or polymerization initiator to provide for the polymer composition. The specific manner of polymerization is not critical and the polymerization techniques employed do not form a part of this invention. In order to maintain solubility in the biocompatible solvent, the polymers described herein are preferably not cross-linked.

In another particularly preferred embodiment of the implant-forming or augmenting solution, the biocompatible polymer composition can be replaced with a biocompatible prepolymer composition containing a biocompatible prepolymer. In this embodiment, the composition comprises a biocompatible prepolymer, an optional biocompatible water insoluble contrast agent preferably having an average particle size of about 10 μm or less and, optionally, a biocompatible solvent.

The term "biocompatible prepolymer" refers to materials which polymerize in situ to form a polymer and which, in the amounts employed, are non-toxic, chemically inert, and substantially non-immunogenic when used internally in the patient and which are substantially insoluble in physiologic liquids. Such a composition is introduced into the body as a mixture of reactive chemicals and thereafter forms a biocompatible polymer within the body. Suitable biocompatible prepolymers include, by way of example, cyanoacrylates, hydroxyethyl methacrylate, silicon prepolymers, and the like. The prepolymer can either be a monomer or a reactive oligomer. Preferably, the biocompatible prepolymer is also non-inflammatory when employed in situ.

Prepolymer compositions can be prepared by adding sufficient amounts of the optional contrast agent to the solution (e.g., liquid prepolymer) to achieve the effective concentration for the complete polymer composition. Preferably, the prepolymer composition will comprise from about 10 to about 40 weight percent of the contrast agent and more preferably from about 20 to about 40 weight percent and even more preferably about 30 weight percent. When the contrast agent is not soluble in the biocompatible prepolymer composition, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm).

When the prepolymer is liquid (as in the case of polyurethanes), the use of a biocompatible solvent is not absolutely necessary but may be preferred to provide for an appropriate viscosity in the implant-forming solution. Preferably, when employed, the biocompatible solvent will comprise from about 10 to about 50 weight percent of the biocompatible prepolymer composition based on the total weight of the prepolymer composition. When a biocompatible solvent is employed, the prepolymeric composition typically comprises from about 90 to about 50 weight percent of the prepolymer based on the total weight of the composition.

In a particularly preferred embodiment, the prepolymer is cyanoacrylate which is preferably employed in the absence of a biocompatible solvent. When so employed, the cyanoacrylate adhesive is selected to have a viscosity of from about 5 to about 20 centipoise at 20° C.

The particular order of addition of components is not critical and stirring of the resulting suspension is conducted as necessary to achieve homogeneity of the composition. Preferably, mixing/stirring of the composition is conducted under an anhydrous atmosphere at ambient pressure. The resulting composition is sterilized and then stored preferably in sealed amber bottles or vials until needed.

Several specific embodiments of implant-forming solutions suitable for use with the apparatus of the present invention are described in U.S. Pat. Nos. 5,667,767 dated Sep. 16, 1997, 5,580,568 dated Dec. 3, 1996, and 5,695,480 dated Dec. 9, 1997 and International Publication Number WO 97/45131 having an International Publication Date of Dec. 4, 1997, the entire content of which is incorporated herein by this reference.

Supply assembly 58 further includes second and third reservoirs in the form of second and third syringes 126 and 128. Second syringe 126 is filled with dimethyl sulfoxide (DMSO) or any other suitable liquid. Third syringe 128 is filled with a saline solution or any other suitable aqueous or physiologic solution.

A manifold assembly or manifold 130 is provided for coupling syringes 118, 126 and 128 to fluid connector 110. In one embodiment, the manifold 130 has a plurality of three stopcocks 132, 134, 136 and a plurality of at least two and as shown a plurality of four ports or Luer fitting portions. A first Luer fitting portion 138 cooperatively mates with forward Luer fitting portion 122 of syringe 118. A second Luer fitting portion 140 cooperatively mates with second Luer fitting portion 84 of fluid connector 110. Third and fourth Luer fitting portions 142 and 144 are additionally provided. Third Luer fitting portion 142 is connected by a tube 146, a portion of which is shown in FIG. 1, to second syringe 126 and fourth Luer fitting portion 108 is connected by a tube 148, a portion of which is shown in FIG. 1, to third syringe 128. Stopcocks 132, 134, 136 operate in a conventional manner to direct fluid flow between Luer fitting portions 138, 140, 142 and 144. In a further embodiment of the invention (not shown), syringe 118 can be secured directly to fluid connector 110 or proximal end portion 96a of needle 96. It should be appreciated that manifold 130 can alternatively be provided with any number of Luer fitting portions or be of any other configuration for coordinating fluid flow from a plurality of syringes or other fluid reservoirs.

Supply assembly 58 further includes a delivery device or gun 150 for supplying a plurality of discrete preselected amounts of the fluid within barrel 120 to needle 96 (see FIGS. 1 and 5). Gun 150 has a cylindrical housing 152 made from plastic or any other suitable material for receiving syringe barrel 120. Housing 152 is formed from a base portion 154 and a cover portion 156 pivotally secured to base portion 154 by hinge 158. A latch 160 is pivotally coupled to cover portion 156 for engaging base portion 154 and thereby locking cover portion 156 in a closed position. Housing 152 has a forward opening 162 for receiving Luer fitting portion 122 of syringe 118. A handle 164 made from plastic or any other suitable material depends from base portion 154. Handle 164 has an internal cavity 166. First and second spaced-apart reinforcing members 168 and 170 extend downwardly from base portion 154 at the front and rear of handle 164. Reinforcing members 168 and 170 are longitudinally aligned and are each provided with a bore 172 extending longitudinally therethrough and opening into internal cavity 166. A rod 174 made from plastic or any other suitable material is slidably disposed within bores 172. Rod 174 has a paddle 176 extending upwardly from the rear thereof perpendicularly to the longitudinal axis of the rod. Paddle 176 is adapted to engage the end of syringe plunger 124. A ring 178 sized for receiving a finger of a human hand extends rearwardly from paddle 176 for facilitating the pulling of rod 174 rearwardly in bores 172.

Rod 174 and paddle 176 are included within the finger operable means of gun 150 for causing incremental relative movement between barrel 120 and plunger 124 of syringe 118. A trigger 180 extends from an opening 182 at the front of handle 164 below rod 174. The trigger is slidably disposed in a direction parallel to the longitudinal axis of rod 174 between first and second spaced-apart guides 184 provided in internal cavity 166. Trigger 180 moves between a first or fully extended position to a second or fully retracted position. A lever 186 is pivotally coupled to handle 164 by means of a pin 188. The lever 186 has a first end portion 186a which extends behind trigger 180 and a second end portion 186b having a wedge-like shape for engaging one of a plurality of longitudinally spaced-apart notches formed in the bottom of rod 174. When trigger 180 is pulled rearwardly by the finger of a human hand, the trigger engages lever first end portion 186a to cause lever 186 to pivot about pin 188 from a first or home position to a second or operational position. Lever second end portion 186b moves forwardly during this half-stroke to engage one of notches 190 and cause rod 174 to move forwardly relative to housing 152. Paddle 176 follows rod 174 and incrementally pushes plunger 124 into barrel 120 for each pull of trigger 180.

A fixed stop 192 is provided in handle 164 for limiting the rearward movement of trigger 180 and thus determining the incremental amount of fluid within barrel 120 dispelled from syringe 118 with each pull of trigger 180. The rearward travel of trigger 180 can be selectively limited by means of one or more additional pins or stops 194, one of which is shown in FIG. 5. Adjustable limit pin 194 is slidably mounted within handle 164 for movement from a first position out of the path of trigger 180 to a second position within the path of trigger 180 so as to selectively limit the rearward stroke of trigger 180 when engaged and placed in its second position.

A coil spring or any other suitable biasing number is provided having one end coupled to a pin mounted within handle 164 and a second end secured to second end portion 186b of lever 186. The coil spring urges lever 186 back to its home position, out of engagement with notches 190, when the finger pressure on trigger 180 is released. The coil spring causes lever first end portion 186a to push trigger 180 outwardly from opening 182 to its home position.

A finger operable adjustment mechanism 196 is connected to needle proximal end portion 96a and sleeve proximal end portion 98a for causing longitudinal relative movement between the needle 96 and sleeve 98. The adjustment mechanism 196 can be of any suitable type for use with any suitable needle assembly having a needle and sleeve which are adjustable relative to each other. One embodiment of such an adjustment mechanism 196 is carried by gun 150. As shown in FIG. 1, such adjustment mechanism 196 has a first or forward post 198 and a second or rear post 200 extending upwardly from the top of cover portion 156. The longitudinally spaced-apart posts 198 and 200 extend perpendicularly to barrel 120. A slidable member or slide bar 202 is slidably mounted in a bore (not shown) provided in forward post 198 for forward and rearward movement in a direction parallel to barrel 120. A thumb screw 204 having an enlarged head 204a is slidably disposed in a bore (not shown) provided in rear post 200. Screw head 204a abuts rear post 200 and the other end of screw 204 is threadably received within the back end of slide bar 202. Counterclockwise rotation of thumb screw 204 relative to rear post 200 causes slide bar 202 to move rearwardly toward forward post 198, while clockwise rotation of thumb screw 204 results in slide bar 202 moving forwardly away from post 198. An L-shaped coupler 206 is pivotally coupled to the forward end of slide bar 202 by means of a pin 208. Coupler 206 has first and second spaced-apart arms 210 forming a slot 212 therebetween for receiving the central portion of grip 112. A screw 214 extends between arms 210 for locking the arms to grip 112 and thus longitudinally locking sleeve 98 relative to needle 96.

Overtube assembly 42 of the present invention includes an elongate tubular member or overtube member 72 (see FIGS. 1-3). Overtube member 72 may be formed of either rigid or flexible materials. For example, overtube member 72 may be formed of rigid plastic tubing, flexible plastic tubing or flexible silicon tubing and can be made from any suitable material such as polyetheretherketone (PEEK), polypropylene (PP) or fluorinated ethylene propylene (FEP). Preferably, overtube member 72 is optically clear and is flexible such that it provides a tight frictional seal against insertion tube 54 at its proximal portion and/or at its distal portion end cap 74. Overtube member 72 includes a proximal end portion 72a and a distal end portion 72b. Overtube assembly 42 has a length preferably approximate the length of insertion tube 54, as for example a length ranging from 100 to 150 centimeters and preferably approximately 125 centimeters, and a diameter ranging from 0.5 to 2.5 centimeters and preferably ranging from 0.75 to 1.5 centimeters. One should appreciate, however, the length of overtube assembly 42 may vary depending upon the size of probe 44, the intended patient and other factors.

The overtube assembly 42 is rotatably mounted on at least a portion of insertion tube 54. A seal 216 having a seal aperture 218 is provided on overtube member 72 and is shown as being provided on the proximal end of the overtube member 72. Insertion tube 54 may be inserted into overtube assembly 42 through seal aperture 218 thereby forming an internal chamber or pressure chamber 68 between insertion tube 54 and overtube assembly 42. A suction source 220 is coupled with overtube assembly 42 via a suction source coupling 222 to produce negative pressure within pressure chamber 68. Suction source 220 may include any well known suction devices such as a suction pump or a conventional 50 cubic centimeter syringe.

Overtube assembly 42 includes an end cap 74 secured to distal end portion 72b of overtube member 72 by any suitable means such as heat sealing, adhesive, threads or press fit. End cap 74 has a length ranging from one to ten centimeters and preferably ranging from two to three centimeters and may be formed by injection molding or machining from any suitable material. The end cap 74 is preferably made from a clear plastic such as polymethylpentene (PMP) or acrylic. The end cap 74 has an outer surface preferably in the form of outer cylindrical surface 224 and an outer diameter approximately equal to the outer diameter of overtube member 72. End cap 74 includes a rounded end or blunt nose 225 which facilitates insertion into and advancement through the gastrointestinal tract thus preventing or minimizing injury to thereto. End cap 74 is provided with a central passageway or bore 223 that communicates with chamber 68 and terminates at an opening formed in blunt nose 225. An optical window 226 made from any suitable material is secured to nose 225 at the opening to enable optical viewing device 48 to provide visual feedback of the gastrointestinal tract beyond end cap 74.

Figure 7:
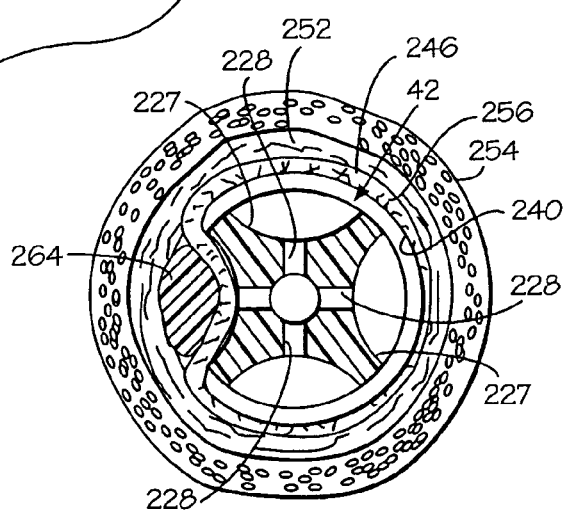
FIG. 7 is a cross-sectional view of the lower esophageal sphincter of FIG. 6 at the level of the gastric cardia taken along the line 7-7 of FIG. 6.

End cap 74 is formed with at least one recess or vacuum cavity 227 that opens onto outer surface 224. One should appreciate that one, two, three, four or more recesses or vacuum cavities 227 may be provided in the distal extremity of overtube assembly 42. Such vacuum cavities can be circumferentially disposed about the end cap, as shown in FIG. 1 where three of four circumferentially spaced-apart cavities 227 are shown and as shown in FIG. 7 where four circumferentially spaced-apart cavities 227 are shown. Each of the vacuum cavities 227 of end cap 74 is elongated and is formed in part by a flat cavity base 229. A peripheral wall 231 serves as the side wall of the vacuum cavity 227. One should appreciate that the size and shape of vacuum cavity may vary in accordance with the medical procedure with which it is used. For example, vacuum cavity may have a semispherical shape. Each vacuum cavity 227 is fluidly connected to pressure chamber 68 by means of at least one passageway 232 which extends from the cavity 227 to central bore 223. Vacuum openings or apertures 228 are located in a portion of end cap 14 which forms a cavity base 229 of each vacuum cavity 227, as shown in FIG. 3, and serve as the openings for respective internal passageways 232 into the vacuum cavity. Each recessed wall or base 229 is provided with a plurality of apertures 228 therein and, more specifically, has a plurality of six apertures arranged in two rows with three apertures in each row. Although base 229 is shown as being planar, it should be appreciated that the base 229 can be nonplanar, such as concave or convex, and be within the scope of the present invention.

Insertion tube 54 extends through overtube member 72 such that distal extremity 54b is adjacent to distal end 72b (see FIGS. 1 and 3). Optical viewing device 48 provides visual feedback about needles 96 when they are extended from distal face 56 of insertion tube 54 into vacuum cavity 227. Overtube assembly 42 may include four vacuum cavities 227 and four corresponding needle guides 234. An identifying reference mark 236 such as a spline may be provided on the inside of overtube member 72 adjacent distal end 72b that is viewable through probe 44 to define a reference point for determining the position of needle 96 with respect to the four vacuum cavities 227. Any other suitable identifying reference mark 236, such as an etched and inked mark on the inside of the overtube member 72, can alternatively be provided. Use of the identifying mark 236 provides a relative position, for example a twelve o'clock position, of probe 44 within overtube assembly 42.

Treatment device 40 can be used for any suitable procedure within the upper gastrointestinal tract, such as the treatment of gastroesophageal reflux disease (GERD). A portion of a human body 238 is shown in FIGS. 6 and 7 and has an internal cavity in the form of esophagus 240 extending through a lower esophageal sphincter 242 to a stomach 244. Such cavity is accessible by a natural body opening in the form of a mouth (not shown) and is defined by an intraluminal wall 232. Esophagus 240 is part of the gastrointestinal tract of body 238 that extends from the mouth to an anus (not shown). An esophageal mucosa 246 serves as the inner layer of intraluminal wall 232 in the esophagus 240 and gastric mucosa 248 serves as the inner layer of the intramural wall 232 in stomach 244. The esophageal mucosa and the gastric mucosa meet at a squamocolumnar junction 250. Wall 232 has a muscle layer comprising layer of circular muscle 252 extending beneath mucosa layers 246 and 248 and layer of longitudinal muscle 254 beneath circular muscle 252. The muscle layers 252 and 254 each extend around esophagus 240 and stomach 244. Wall 232 further includes a submucosal layer or submucosa 256 extending between the mucosa and the muscle layers. A submucosal space, that is a potential space, can be created between mucosa layer 246 or 248 and circular muscle layer 252 by the separation of layer 246 or 248 from muscle layer 252. In addition, as with any muscle, wall 232 includes an intramuscular potential space, that is a space which can be created intramuscularly by distension and separation of muscle fibers within a single muscle or between layers of muscle. Wall 232 has a depth or thickness which includes at least mucosa layers 246 and 248, muscle layers 252 and 254 and submucosa 256. A phreno-esophageal ligament 258 and a diaphragm 260 extend around esophagus 240 above lower esophageal sphincter 242.

In one method of the present invention, at least one implant-forming solution is introduced into the wall 232 of the gastrointestinal tract to form at least one implant 264 in the wall 232 of the gastrointestinal tract. In one preferred method of operation and use, the apparatus of the present invention is used to inject the implant-forming solution into a portion of a wall forming a cavity in a body in a procedure similar to that disclosed in U.S. Pat. No. 6,251,063, the entire content of which is incorporated herein by this reference. In particular, overtube assembly 42 and treatment device 40 are used in accordance with the present invention to form a protrusion 230 in a portion of wall 232 into which an implant-forming solution is injected.

In one embodiment, syringe 118 is filled with the implant-forming solution in preparation of the procedure. Syringe 118 is loaded into gun 150 by opening cover portion 156 to permit placement of barrel 120 within housing 152. Ring 178 is grasped to pull rod 174 rearwardly relative to housing 152 so that paddle 176 is disposed behind the retracted plunger 124.

Cover portion 156 is closed and secured to base portion 154 by means of latch 160. The physician thereafter pulls trigger 180 as necessary to cause paddle 176 to engage the rear of plunger 124.

Supply assembly 58 is attached to needle assembly 52 after needle 96 and sleeve 98 have been disposed in working channel 88 of probe 44. Alternatively, supply assembly 52 can be attached to the needle assembly prior to such disposition of the needle assembly within probe 44. In either case, attachment is accomplished by coupling first Luer fitting portion 138 of manifold 130 to Luer fitting portion 122 of syringe 118 and second Luer fitting portion 106 of the manifold to first Luer fitting portion 156 of fluid connector 110. Coupler 206 is pivoted downwardly so that first and second arms 176 thereof engage grip 112 and screw 179 tightened to secure grip 112 in slot 178 between arms 176. Thumb screw 204 is rotated in a counterclockwise direction relative to rear post 186 to ensure that needle 96 is fully retracted within sleeve 98. Thereafter, saline solution syringe 128 is coupled by means of tube 148 to third Luer fitting portion 142 of manifold 130 and DMSO syringe 126 is coupled by means of tube 146 to fourth Luer fitting portion 144 of the manifold.

Probe 44 is prepared by connecting light cable 84 to light source 86 and attaching the proper eyepiece 76 to probe handle 62. In addition, all other conventional attachments are applied to probe 44. Insertion tube 54 is then inserted within overtube assembly 42 via aperture 218 of seal 216.

After the patient has been appropriately sedated or anesthetized, probe handle 62 is grasped by the physician to introduce distal end 72b of overtube assembly 42 and distal extremity 54b of probe 44 into the mouth of the patient and to advance overtube assembly 42 with insertion tube 54 down esophagus 240. Optical viewing device 48 facilitates advancement by the physician of the insertion tube 54 and the overtube assembly 42. In addition, the optical viewing device 48 enables the physician to ensure that overtube assembly 42 is properly disposed within esophagus 240. Insertion tube 54 and overtube assembly 42 each have a length so that when distal extremity 54b and distal end 72b are in the vicinity of lower esophageal sphincter 242, proximal extremity 54a and proximal end 72a are outside of body 238. The optically clear material of end cap 74 permits light from light guides 82 to illuminate the esophagus and thus enhance visualization by optical viewing device 48 through window 226.

Although the method of positioning overtube assembly 42 within the esophagus is described herein as utilizing an optical viewing device, it should be appreciated that the overtube assembly can be introduced into the esophagus without the aid of an optical viewing device. For example, the overtube assembly 42 can be positioned in the esophagus by merely introducing the distal end of the overtube assembly a predetermined distance to the desired treatment site. The insertion distance of overtube assembly 42 can be measured by external observation of the proximal extremity of assembly and optionally by gradations (not shown) provided on the outer surface of such proximal extremity.

A portion of the procedure for treating wall 232 in the vicinity of lower esophageal sphincter 242 is shown in FIG. 6. Under the guidance of optical viewing device 48, which has a field of view forward distal face 56 of insertion tube 54 and forward of overtube assembly 42 through optical window 226, overtube assembly 42 is maneuvered to a position such that at least one vacuum cavity 227 is adjacent the portion of wall 232 which is to be treated. Suction source 220 is then activated to draw air from and evacuate pressure chamber 68 of overtube assembly 42. A negative pressure is thus created within the pressure chamber 68 and the vacuum cavities 227. This negative pressure creates a suction effect which draws targeted tissue, that is a portion of wall 232 to be treated, into vacuum cavity 227 to form a protrusion 230 in the targeted tissue, as shown in FIG. 6. It should be appreciated that FIGS. 6 and 7 are somewhat schematic and that, in this regard, the size of esophagus 240 has been exaggerated relative to the size of insertion tube 54 and overtube 72 in FIG. 6. The sizing of esophagus 240 relative to insertion tube 54 and overtube 72 are more accurate in FIG. 7.

Distal end portions 96b and 98b of needle assembly 52 are now advanced until such distal end portions of needle 96 and sleeve 98 are in the vicinity of insertion tube distal extremity 54b, overtube distal end 72b and end cap 74. Needle 96 and sleeve 98 are each movable from a first position in which distal end portions 96b and 98b are each retracted within insertion tube 54 and thus recessed within working channel 88 to a second position in which the distal end portions 96b and 98b extend distally beyond the end of insertion tube 54. The needle and sleeve each have a sufficient length so that the physician holding gun 150 can extend both the needle and the sleeve distally from distal extremity 54b. The physician retracts sleeve 98 relative to needle 96 by means of adjustment mechanism 196 so that needle distal end portion 96b extends beyond sleeve distal end portion 98b a selected amount of at least two millimeters and preferably ranging from two to 15 millimeters. Such amount of extension can be easily determined for example by correlating such extension as a function of the rotation of thumb screw 204 and properly calibrating the position of thumb screw 204 relative to rear post 200 in this regard.

The physician primes needle 96 with the saline or other aqueous or physiologic solution from syringe 128 and ensures that needle passage 100 is filled with saline solution by observing with optical viewing device 48 the saline solution being dispelled from the one or more openings 108 in needle distal end portion 96b. For simplicity, the operation of conventional stopcocks 132, 134, 136 for directing appropriate fluids to and from needle passage 100 will not be discussed in connection with the procedure.

The physician advances sleeve 98 and needle 96 distally from insertion tube distal extremity 54b into a respective needle guide 234 such that sleeve 98 and needle 96 are proximate to the protrusion 230. The physician extends needle 96 through needle guide 234 into vacuum cavity 227, which is occupied by the portion of wall 232 to be treated, by moving the needle 96 and sleeve 98 closer to side port 90. This causes sharpened end 104 of needle 96 to penetrate protrusion 230 of wall 232. The field of view of optical viewing device 48 permits the physician to observe movement of needle 96 into needle opening or guide 234 and, in some cases, penetration of protrusion 230. The optically clear material of end cap 74 permits light guides 82 to enhance such visualization. It is noted that the amount of extension of needle 96 into vacuum cavity 227 can be determined for example by correlating such extension as a function of the rotation of thumb screw 204 and properly calibrating the position of thumb screw 204 in relation to rear post 200, as discussed above.

Saline solution may be injected into wall 232 to cause esophageal mucosa 246 or gastric mucosa 248, as the case may be, to separate from circular muscle 252 and further enlarge protrusion 230 in wall 232 providing an internal space 262 filled with the saline solution. The amount of saline solution required to create space 262 can range from 0.25 to ten cubic centimeters and preferably range from one to three cubic centimeters. The physician then retracts needle 96 from space 262, cavity 227 and guide 234 and withdraws the remaining saline solution from passage 100 by means of pulling back the plunger on syringe 128 or by any other suitable method. The physician next cleanses needle passage 100 with DMSO from syringe 126 to ensure that the saline solution has been removed from passage 100. DMSO cleansing can be determined by observing a slight amount of DMSO being dispelled from needle distal end portion 96b. This cleansing step is enhanced by the introduction of the DMSO downstream of saline stopcock 103 and upstream of implant-forming solution stopcock 101. The DMSO is now removed from passage 100 by withdrawing the plunger of syringe 126 or by any other suitable means. Removal of the saline solution from passage 100 and the cleansing of the passage with DMSO inhibits premature precipitation within syringe 118 of the biocompatible polymer in the implant-forming solution from the DMSO in the implant-forming solution. Needle passage 100 is next primed with the implant-forming solution carried by syringe 118 until such solution is available at the openings 108 in needle distal end portion 96b.

The physician again positions insertion tube distal extremity 54b within overtube assembly 42 such that needle 96 aligns with needle guide 234 and causes needle distal end portion 96b to extend through needle guide 234 and penetrate protrusion 230 and extend into space 262. Thereafter, the physician pulls trigger 180 to cause the desired preselected amount of implant-forming solution to be introduced through needle 96 extending through probe 44 into space 262. The openings 108 in needle distal end portion 96b are positioned so that the implant-forming solution is preferably introduced into the middle of space 262. The contrast agent within the implant-forming solution permits the viewing of the implant-forming solution by means of fluoroscopy. In addition, the introduction of the implant-forming solution into wall 232 can be monitored transabdominally or transesophageally by ultrasound. The rate of injection of the implant-forming solution into space 262 can range from 0.1 cubic centimeters per minute to ten cubic centimeters per minute.

Once the implant-forming solution has been introduced into wall 232, the biocompatible polymer of the implant-forming solution precipitates to form one or more discrete deposits or solid implants 264 (see FIG. 6). The amount or bolus of implant-forming solution injected into wall 232 for each implant can range from 0.05 cubic centimeters to 10 cubic centimeters. The ratio of implant-forming solution to saline in space 262 can range from 2:1 to 1:8 and preferably range from approximately one part implant-forming solution to two to three parts saline solution. In one embodiment, space 262 created by the saline solution predefines the configuration of the precipitant or implant 264. As can be seen from FIG. 6, the discrete implant 264 shown therein occupies less than all of space 262. In another embodiment (not shown), more implant-forming solution than saline is introduced into wall 232 so that the discrete implant 264 more than fills the space 262 created by the saline.

An injection of a suitable aqueous or physiologic solution such as a saline solution into wall 232 prior to the injection of the implant-forming solution creates a space 262 which pushes wall 232 against vacuum cavity 227. The injection of the implant-forming solution into the saline filled space 262 facilitates rapid precipitation and enhanced solidification of the biocompatible polymer. This rapid solidification facilitates the desired shaping of implant 264, which is shown in FIG. 6 as being somewhat spherical and elongated in shape and as substantially corresponding to the shape of vacuum cavity 227. It has also been found that the saline solution facilitates the creation of a relatively soft and spongy implant 264. After completion of the injection of implant-forming solution and the solidification of the biocompatible polymer, the remaining solution within space 262 disperses within body 238 and the space 262 contracts about implant 264 (see FIG. 7).

Although only a single implant 264 in wall 232 in the vicinity of the lower esophageal sphincter 242 is shown in FIGS. 6 and 7, additional implants may be created in wall 232. In preparation thereof, needle 96 is removed from protrusion 230, vacuum cavity 227 and needle guide 234, and the implant-forming solution within passage 100 withdrawn by pulling back on plunger 124. The needle 96 is cleansed with DMSO by filling the needle passage 100 with DMSO from syringe 128 and thereafter withdrawing the DMSO from the passage 100. After the subsequent priming needle passage 100 with saline solution from syringe 128, the physician positions overtube assembly 42 within the gastrointestinal tract so that the desired recess 227 is disposed against the desired portion of wall 232. Insertion tube distal extremity 54b is then positioned within overtube assembly 42 such that needle 96 aligns with the needle guide 234 corresponding to such cavity 227 and the procedure discussed above is repeated thus creating one or more additional implants 229. The physician may rotate probe 44 with insertion tube 54 with respect to overtube assembly 42 to align needle 96 with the desired needle guide 234, such as second needle guide 234' shown in FIG. 6 if vacuum cavity 227' is positioned against the portion of wall 232 to be treated.

The number and configurations of implants 229 formed in wall 232 can vary. Specific examples of implant configurations are disclosed in co-pending U.S. Pat. No. 6,251,063. For example, a plurality of circumferentially spaced-apart implants (not shown) may be created in wall 232 below lower esophageal sphincter 242 and below squamocolumnar junction 250. The implants may be disposed substantially in a plane extending perpendicularly to a longitudinal axis extending along the centerline of esophagus 240 and into the stomach 244. The implants may be also be substantially equally spaced apart around the centerline, for example, at approximately 90° intervals in the case of four implants. It should be appreciated, however, that less than four or greater than four implants can be provided and can be circumferentially spaced apart at approximately equal angular intervals or asymmetrically disposed about the center line. The plane of implants can be disposed above, below and/or at the lower esophageal sphincter 242.

In other embodiments, implants can be formed which are not disposed in a single plane. Furthermore, the sizing, spacing and configuration of implants determines whether the esophagus is augmented or partially or completely coapted. A plurality of implants may also be formed in additional planes spaced apart from a first plane of implants. Such an array of implants can be longitudinally centered on the squamocolumnar junction. In another embodiment, a single implant can be provided for augmenting or partially or completely coapting esophagus in the vicinity of the lower esophageal sphincter.

It should be appreciated that one or more implants can be formed in portions of the wall other than the mucosal layers. For example, one or more implants can be formed in one or both of or between the muscle layers 252 and 254. Such implants can serve to augment or partially or completely coapt the esophagus in the vicinity of the lower esophageal sphincter and can also serve to reduce the distensibility of the muscle layers. Implants formed within or between muscle layers 252 and 254 can be arranged in a variety of configurations, including any of the various configuration of implants described above.

The implants created by the apparatus of the invention can add bulk to wall 232 so as to form a barrier between the stomach and the esophagus and/or, if introduced into one or both of the muscle layers 252 and 254 of the wall 232, can serve to reduce the distensibility of such muscle layers 252 and 254 and thereby increase the resistance of the wall 232 in the vicinity of the lower esophageal sphincter 242. Implants can also be formed in wall 232 to form a valve-like mechanism as disclosed in copending U.S. Pat. No. 6,251,064, the entire content of which is incorporated herein by this reference.

Although the method of the invention has been described as including the formation of a space 262 by a saline solution injected into the wall 232 prior to an injection of implant-forming solution into wall 232, it should be appreciated that space 262 can be formed by other aqueous or physiologic solutions or by a local anesthetic. It is also noted that injection of an aqueous or other solution prior to injection of the implant-forming solution is not essential. It is within the scope of the present invention, for example, to inject the implant-forming solution directly into the protrusion 230 without the prior formation of a space 262 by an injection of saline solution or otherwise. The implant-forming solution can also be injected directly into wall 232 without an injection of saline or any other solution for any secondary purpose described herein or otherwise. A saline or other aqueous or physiologic solution can optionally be introduced into such a space formed by the implant-forming solution, that is after the introduction of the implant-forming solution into wall 232, to facilitate dispersion of the DMSO or other biocompatible solvent present in the implant-forming solution. It can thus be seen that the invention is broad enough to cover the introduction of any conditioning solution into the tissue before, during or after the treatment to facilitate the treatment.

In an alternative method for forming a plurality of implants within wall 232, a plurality of spaces 262 can be formed by saline solution from syringe 128. Subsequently, the implant-forming solution from syringe 118 can be sequentially injected into each of such spaces.

It should be appreciated that the implants of the present invention can be used as delivery vehicles for other materials such as radioisotopes, chemotherapeutic agents, anti-inflammatory agents and/or antibiotics. In addition, treatment device 40 can be used for forming implants from other suitable materials in wall 232 of a body. Such materials include suitable suspensions such as injectable bioglass of the type described in Walker et al., "Injectable Bioglass as a Potential Substitute for Injectable Polytetrafluorethylene Particles", J. Urol., 148:645-7, 1992, small particle species such as polytetrafluoroethylene (PTFE) particles in glycerine such as Polytef®, biocompatible compositions comprising discrete, polymeric and silicone rubber bodies such as described in U.S. Pat. Nos. 5,007,940, 5,158,573 and 5,116,387 to Berg and biocompatible compositions comprising carbon coated beads such as disclosed in U.S. Pat. No. 5,451,406 to Lawin. Such suitable materials for forming implants further include collagen and other biodegradable material of the type disclosed in U.S. Pat. No. 4,803,075 to Wallace et al. and other known injectable materials.

The optional contrast agent in the implants permits the implants to be monitored after completion of the procedure described above. Thus the stability of the implant and its configuration can be observed over time. Further procedures can be performed to supplement previously formed implants.

The apparatus for use with the implant-forming solution described above can be used in other gastrointestinal procedures for other than the treatment of gastroesophageal reflux disease and be within the scope of the present invention. For example, the apparatus can be used to augment luminal walls in the vicinity of fistulas to aid in the stenting or other treatment of fistulas as disclosed in copending U.S. Pat. No. 6,248,058, the entire content of which is incorporated herein by this reference. The apparatus also has applications for the treatment of veins and arteries as disclosed in copending U.S. Pat. No. 6,234,955, the entire content of which is incorporated herein by this reference. In this regard, a modified apparatus could be used to inject a solution into veins in the lower esophagus to treat esophageal varices and into veins in the vicinity of ulcers to treat for example gastric ulcers. In addition, similar apparatus can be used to bulk other muscles in a body such as muscles in the vicinity of the anal sphincter to treat incompetent anal sphincters as disclosed in copending U.S. Pat. No. 6,251,063, the entire content of which is incorporated herein by this reference. Similarly, the apparatus can be used for the treatment of hemorrhoids.

The present invention encompasses a minimally invasive apparatus to shape a portion of a wall forming a cavity in a body to be treated, that is to shape targeted tissue of the wall for injecting a material therein. Vacuum cavities 227 advantageously allow a physician to shape the target tissue into protrusions 230 and form implants 264 in the protrusions which have a consistent and predetermined size and shape. The ability to provide consistently sized and shaped implants 264 contributes to the repeatability of the procedure.

It is noted that needle 96 can be provided with a plurality of lumens or passages (not shown) extending longitudinally therethrough for permitting multiple liquids to be separately carried by the needle. In a further alternative embodiment, a plurality of needles (not shown) can be introduced through the working channels of a suitable probe such as probe 44. Each of the needles can be used in combination with an overtube assembly in accordance with the invention. For example, separate needles can be provided for the introduction of the saline solution or other physiologic or aqueous solution, for the introduction of the DMSO or other biocompatible solvent, and for the introduction of the implant forming solution into a protrusion 230 formed in a portion of the wall 232 of the gastrointestinal tract. In yet a further alternative embodiment, a plurality of needles in a single needle assembly can be introduced through a single working channel (not shown) of probe 54. The inclusion of multiple needles reduces the complexity of the procedure because the implant forming solution and saline solution are no longer introduced through the same needle. Thus, for example, the DMSO priming step may be eliminated.

The structure of the overtube assembly and the probe may vary and be within the scope of the present invention. In another embodiment, a plurality of needles may be provided in either the insertion tube and/or the overtube assembly. For example, a modified overtube assembly 266 which includes four needles 268, 269, 270 and 271 as shown in FIGS. 8-11. Overtube assembly 266 has proximal and distal extremities 266a and 266b and is similar to overtube assembly 72; like reference numerals have been used to describe like components of overtube assemblies 72 and 266. Overtube assembly 266 has an overtube member 276 which is substantially similar to overtube member 72 and an end cap 280 mounted on the distal end of the overtube member 276. The proximal end of end cap 280 is provided with an annular recess 282 for receiving the distal end of the overtube member 276 (see FIG. 9). End cap 280 may be attached to the overtube member 276 by any suitable means such as an adhesive or heat shrinking or by means of a pressure fit, snap fit or screw fit. The end cap 280, like end cap 74, is provided with at least one and as shown a plurality of four circumferentially spaced-apart recesses 227 formed by base 229 and peripheral wall 231. A plurality of apertures 228 are formed in a pattern on base 229 and extend therethrough for communicating the vacuum cavity 227 with internal chamber 68 of overtube member 276 by means of passageways (not shown). End cap 280 can be formed integral with overtube member 276, like end cap 74 discussed above, and be within the scope of the present invention.

Figure 8:
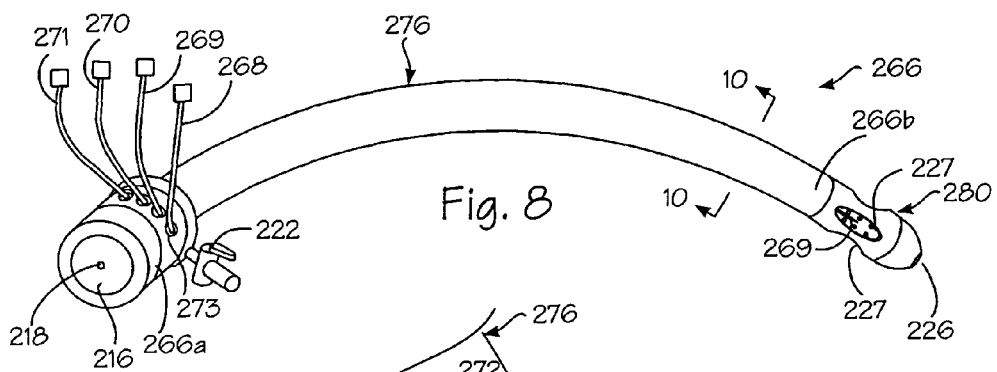
FIG. 8 is a perspective view of another embodiment of a portion of the apparatus of the present invention.
Figures 9, 10, 11:
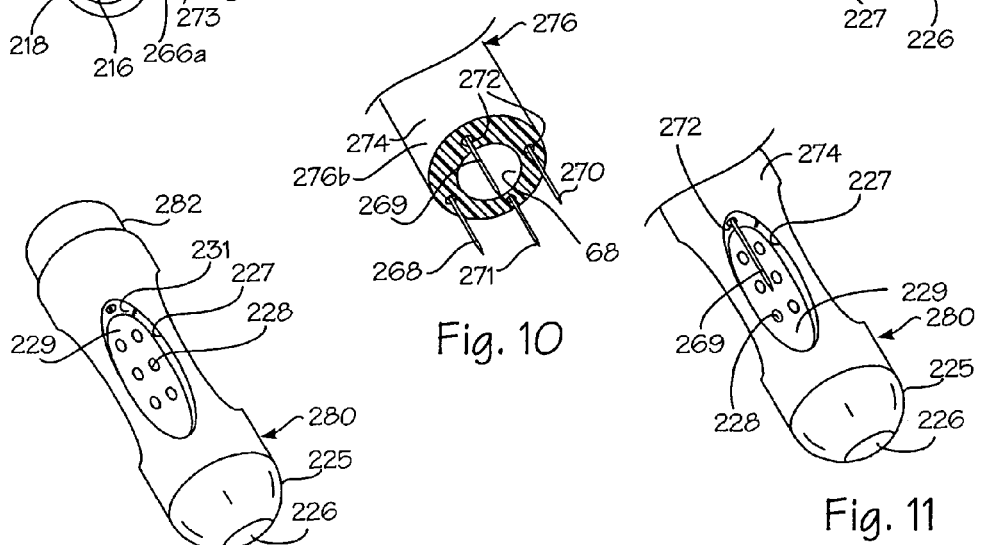
FIG. 9 is an enlarged perspective view, broken apart, of the distal end of the apparatus of FIG. 8.
FIG. 10 is a cross-sectional view of the apparatus of FIG. 8 taken along the line 10-10 of FIG. 8.
FIG. 11 is an enlarged perspective view of the distal portion of the apparatus of FIG. 8.
Figures 12, 13, 14:
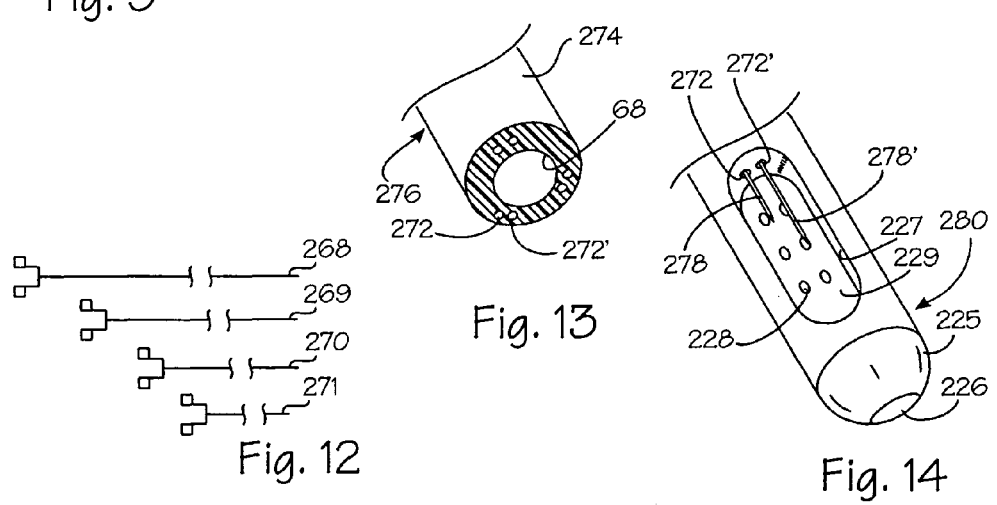
FIG. 12 is a schematic view of a plurality of needles for use in the apparatus of FIG. 8.
FIG. 13 is a cross-sectional view, similar to FIG. 10, of a further embodiment of the apparatus of the present invention.
FIG. 14 is an enlarged perspective view, similar to FIG. 11, of the distal portion of the apparatus of FIG. 13.

Each of needles 268-271, which are preferably slidably disposed within respective sleeves 98 (not shown), extends through a respective passageway or lumen 272 located in side wall 274 of overtube member 276 (see FIG. 10). The needles each enter the respective lumen 272 through a needle port 273 located in the proximal end 266a of overtube assembly 266, as shown in FIG. 8. Although the four needle ports 273 are shown in FIG. 8 to be asymmetrically spaced apart in close proximity to each other, one should appreciate that overtube assembly 266 can be provided with a varying number of needle ports which can be asymmetrically or symmetrically spaced about proximal end 266a. Side wall lumens 272 extend through side wall 274 of overtube member 276 and terminate in respective vacuum cavities 227 (see FIG. 11). The four lumens 272 are angularly spaced apart about a longitudinal axis of overtube member 276 at distal extremity 266b to correspond to the respective vacuum cavities 227. In the embodiment of FIGS. 8-11, proximal end 266a includes a conventional fitting which direct needles 268-271 from the asymmetrically spaced-apart ports 273 to the symmetrically spaced-apart lumens 272 provided in side wall 274 of the overtube member 276. Needles 268-271 are preferably provided with equal lengths, although the needles 268-271 can having varying lengths as shown in FIG. 12. FIG. 10 shows lumens 272 symmetrically spaced around the longitudinal axis of overtube member 276, but it should be appreciated that lumens 272 may be asymmetrically spaced about the longitudinal axis.

Needles 268-271 of varying lengths, as shown schematically in FIG. 12, can be provided to assist the operating physician in identifying the individual the needles within the body. For example, a longer needle may be provided at a relative twelve o'clock position and a shorter needle may be provided at a relative three o'clock position, such positions being readily discernable by the physician when the needles are inserted equally into apparatus 40. Alternatively, the needles may be differently colored or provided with other indicia to assist in their respective identification. Needles of various lengths may be used in combination with an identifying mark to assist in identifying the needles within the body and to determine their relative position with respect to the overtube. Such an identifying mark 236, shown in FIG. 3, provides a position within the overtube assembly 42 from which the position of a needle can be ascertained. With respect to FIG. 10, for example, needle 270 could be positioned at the twelve o'clock position adjacent the identifying mark, not shown in FIG. 10, and thus needle 271 would be positioned at the three o'clock position, needle 268 at the six o'clock position, and needle 269 at the nine o'clock position. The lengths of the extensions of the needles as they are oriented at distal end 276b of overtube member 276 clarify their spatial position when viewed with reference to the identifying mark located within overtube assembly 266. It should be appreciated that an overtube assembly having needles of various lengths and/or colors can be provided without an identifying mark.

The use and operation of the embodiment of FIGS. 8-12 is similar to that of the first embodiment discussed above. For example, overtube assembly 266 is of a length such that when distal end portion 266b is in the vicinity of the lower esophageal sphincter, proximal end portion 266a is outside the body allowing the physician to manipulate needles 268-271. The provision of several needles is advantageous in that a separate needle may be dedicated to each vacuum cavity 227 thus eliminating the need to successively align a probe needle with a corresponding needle guide of several vacuum cavities.

In another embodiment, shown in FIGS. 13 and 14, overtube member 274 includes pairs of parallel lumens which together terminate in a respective vacuum cavity 227. More specifically, overtube member 276 therein has pairs of lumens 272, 272' which extend through side wall 274 in parallel and terminate in a single vacuum cavity 227. A pair of needles 278, 278' extends through a corresponding pair of lumens 272, 272' and are insertable into the corresponding vacuum cavity 227, as shown in FIG. 14. An advantage of this embodiment is that each needle may be dedicated to a single solution, thus eliminating the need to re-prime the needles. For example, needle 278 may be dedicated to the saline solution in syringe 128 and needle 278' may be dedicated to the DMSO in syringe 126.

Figure 15:
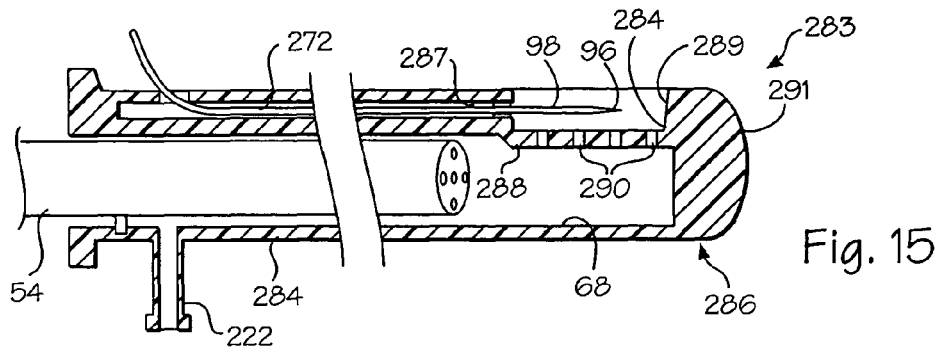
FIG. 15 is a cross-sectional view of the distal portion of yet another embodiment of the apparatus of the present invention.

In a further embodiment, an overtube assembly 283 having a single vacuum cavity 284 can be provided. Overtube assembly 283, shown in FIG. 15, is substantially similar to overtube assembly 266 and like reference numerals have been used to describe like components of overtube assemblies 266 and 283. An overtube member 285, similar to overtube member 276, and an end cap 286 are included in assembly 283. End cap 286 can be formed by any suitable means, such as injection molding, and is preferably made from an optically clear material. The end cap 286 has a length ranging from one to ten centimeters and preferably ranging from one to three centimeters and is secured to overtube member 285 by any suitable means such as an adhesive (not shown). The end cap has an outer cylindrical wall, in which single recessed portion or recess 284 is formed, and is provided with a longitudinally-extending lumen 287 which communicates with sidewall lumen 272 of overtube member 285. Lumen 287 terminates in vacuum cavity 284, which is formed by a base 288 and a peripheral wall 289. A plurality of passageways or apertures 290 extend through base 288 and communicate with internal chamber 68 of the overtube assembly 283. The apertures 290 are arranged in a pattern of four longitudinally-extending rows with two apertures in each row. A needle 96 with a protective sleeve 98 extends through lumens 272 and 287 and is accessible at the proximal extremity of overtube assembly for movement into and out of the vacuum cavity 284. End cap 286 is formed with a blunt, rounded nose 291 that is closed.

As discussed above with respect to end cap 74, the optically clear material of end cap 286 enhances visualization by permitting illumination of the esophagus with light guides 82. Such light enhances the clarity of the image received by optical viewing device 48. The relatively short length of the end cap 286 and the relatively large diameter of pressure chamber 68 distal of insertion tube 54 permit optical viewing device 48 to have a relatively large field of view looking distally of the end cap 286. The shape of the end cap nose contributes to the type of image available to viewing device 48. In the embodiment of FIG. 15, rounded, convex nose 291 magnifies the image viewed by optical device 48.

Figure 16:
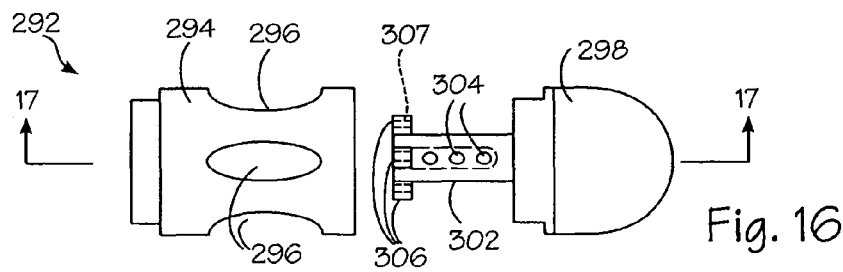
FIG. 16 is an exploded view of a distal portion of yet a further embodiment of the apparatus of the present invention.

The end cap of the present invention may be formed of multiple components. In the embodiment illustrated in FIG. 16, an end cap 292 is provided that is mountable in the manner discussed above with respect to end cap 280 to an overtube member similar to those discussed above. Alternatively, end cap 280 can be a separate piece, like end cap 332 discussed below, that is removably mounted to insertion tube 54 by any suitable means such as discussed below with respect to end cap 332. End cap 292 has a cylindrical sleeve member 294 in which at least one and as shown a plurality of openings 297 are formed for providing an equal plurality of vacuum recesses 297 in the end cap. Sleeve member 294 receives an inner cylindrical portion 302 of an end piece 298. Cylindrical portion 302 serves as the base for the vacuum recesses or cavities 297 of end cap 292. Vacuum apertures 304 are formed within and extend through cylindrical portion 302 for providing suction to vacuum cavities 297. A needle guide 306 extends radially outwardly from inner cylindrical portion 302 for each of the vacuum cavities and is formed with an opening 307 extending therethrough for guiding the respective needle 96 and sleeve 98 carried within insertion tube 54 toward vacuum recess 296.

Figure 17:
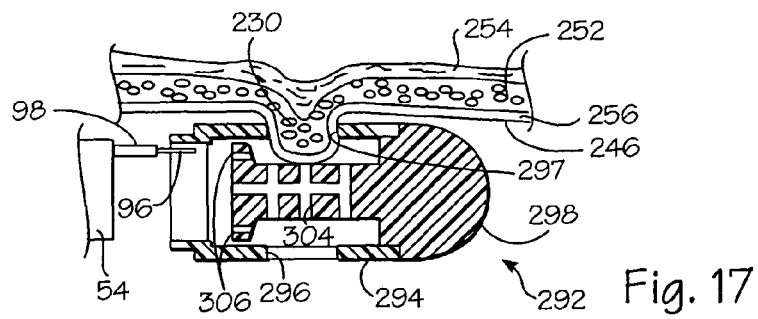
FIG. 17 is a cross-sectional and partially exploded view of the distal portion of FIG. 16, shown treating a portion of a wall of a cavity in accordance with the present invention, taken along line 17-17 of FIG. 16.

In the operation of end cap 292, shown in FIG. 17, a protrusion 230 is formed in a vacuum cavity 297 in the manner discussed above. The operating physician then extends needle 96 into the protrusion to form an implant 264 and thus treat wall 232. The protrusion 230 can be visualized with optical viewing device 48 during needle injection.

Figure 18:
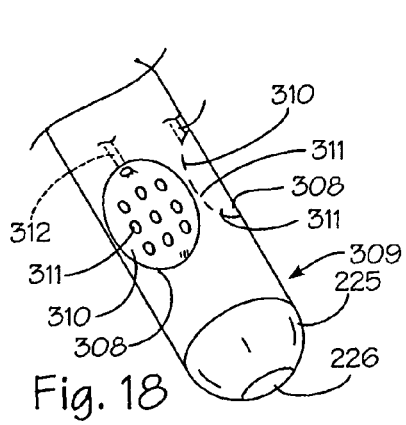
FIG. 18 is an enlarged perspective view, similar to FIG. 11, of a distal portion of another embodiment of the apparatus of the present invention.

It should be appreciated that the vacuum cavity described herein may take the form of different shapes or geometries in order to form protrusions of various desired shapes or geometries. An end cap 309, for example being substantially similar to any of the end caps 74, 280 or 286 described above, can be provided with one or more recesses or vacuum cavities 308 that are substantially semispherical in shape (see FIG. 18). Like reference numerals have been used to describe like components of end caps 74, 280, 286 and 309. Each of the openings or recesses 308 is substantially circular in cross section and is formed by a wall 310 that is substantially circular in cross section. An array of openings 311 are provided in wall 310 of each recessed portion or vacuum cavity 308. The openings 311 communicate with a vacuum source (not shown) by means of a passageway or lumen (not shown) provided in the end cap 309. A needle (not shown), for example similar to needle 96 described above, is insertable into each of the vacuum cavities 308 by means of a passageway or needle guide 312.

Figure 19:
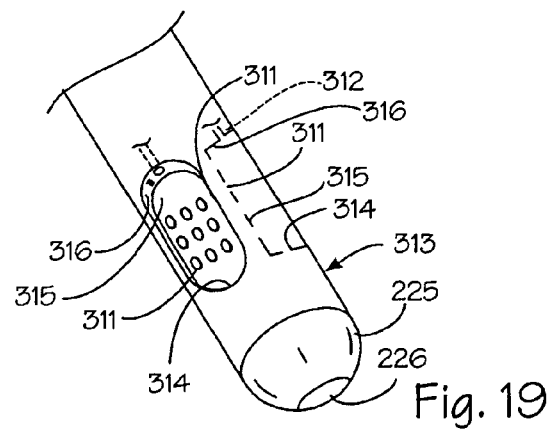
FIG. 19 is an enlarged perspective view, similar to FIG. 18, of a distal portion of a further apparatus of the present invention.

In a further embodiment, an end cap 313 having at least one recess or vacuum cavity 314 that is elongated or elliptical can be provided (see FIG. 19). End cap 313 is substantially similar to end cap 309 and like reference numerals have been used to describe like components of end caps 309 and 313. As shown, a plurality of vacuum cavities 314 are provided in end cap 313. Each of the elliptically-shaped vacuum cavities is formed by a substantially planar base 315 and a peripheral side wall 316 that is substantially elliptical in shape.

Figure 20:
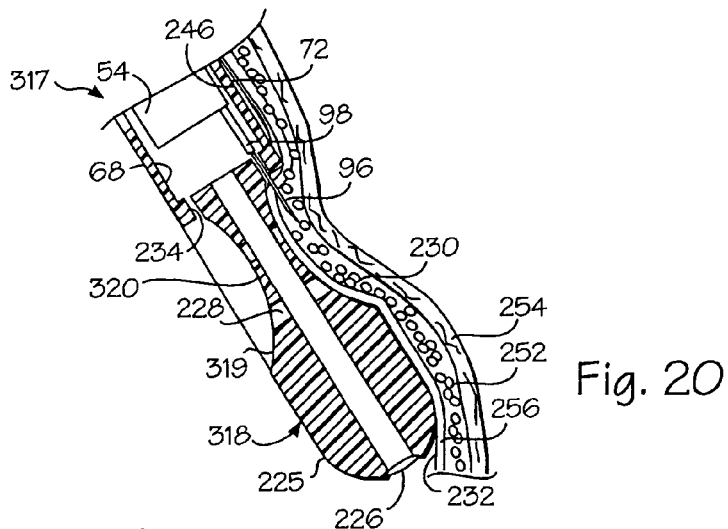
FIG. 20 is an enlarged cross-sectional view, similar to FIG. 3, of a distal portion of another embodiment of the apparatus of the present invention shown treating a portion of a wall of a cavity in accordance with the present invention.

An overtube assembly 317 substantially similar to overtube assembly 42 is shown in FIG. 20, where like reference numerals have been used to describe like components of overtube assemblies 42 and 317. The overtube assembly has an end cap 318 secured to the distal end of overtube member 72, which end cap 318 is more particularly shown as being formed integral with the overtube member 72. At least one and as shown a plurality of recesses or vacuum cavities 319 are formed in the outer cylindrical wall of end cap 318. More specifically, overtube assembly 317 has a plurality of four vacuum cavities 319 circumferentially spaced apart about the longitudinal axis of the overtube assembly 317 at equal separation angles of 90°. Each of the vacuum cavities is formed by an arcuate, concave wall 320, that gently curves substantially the entire length of the vacuum cavity, so as to have a shape which resembles half of a teardrop.

The operation and use of overtube assembly 317 is similar to the procedure discussed above with respect to overtube assembly 42. After overtube assembly 317 and probe 54 have been properly positioned within the gastrointestinal tract with one of the vacuum cavities 319 disposed adjacent the targeted tissue, suction source 220 is activated by the operating physician to provide a negative pressure in chamber 68 and each of vacuum recesses 318 and thus draw a portion of wall 232 into the desired vacuum cavity 319. A protrusion 230 is thereby formed in such vacuum cavity that has substantially the shape of the vacuum cavity (see FIG. 20). Needle 96 is inserted through the respective needle guide 234 and into the vacuum cavity to penetrate the protrusion 230 and form an implant within the protrusion. Needle 96 is shown penetrating circular muscle layer 252 in FIG. 20, prior to the injection of the implant-forming solution into the protrusion. The arcuate shape of recess wall 320 influences the cross-sectional shape of the implant so formed in wall 232.

As can be seen, differently shaped vacuum cavities or recesses can be used to form protrusions 230 of various shapes. For example, cavity recess 308 shown in FIG. 18 can be used to form a substantially semispherical-shaped protrusion and thus a similarly shaped implant. It should be appreciated from the foregoing that a multitude of other cavity shapes and profiles may be used in accordance with the present invention. For example, other end caps can be provided with one or more vacuum recesses having the shape of a square or rectangle.

Figure 21:
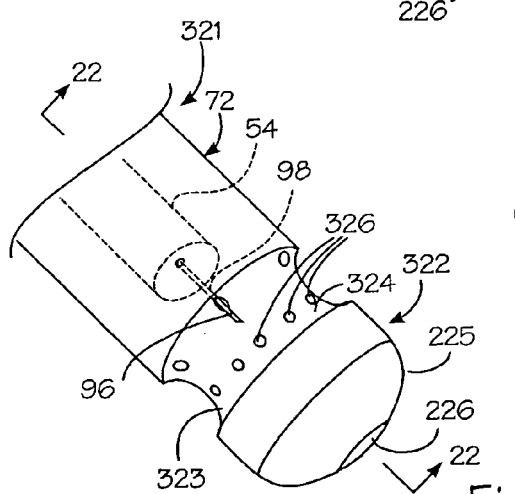
FIG. 21 is an enlarged perspective view, similar to FIG. 11, of a distal portion of a further embodiment of the apparatus of the present invention.
Figure 22:
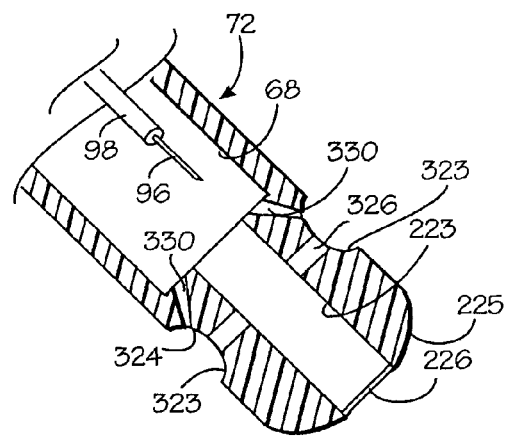
FIG. 22 is a cross-sectional view of the distal portion of FIG. 21 taken along line 22-22 of FIG. 21.

Apparatus of the present invention can also be provided with vacuum cavities that extend circumferentially around the distal portion of the apparatus. The distal portion of an overtube assembly 321, substantially similar to overtube assembly 42, is shown in FIGS. 21 and 22. Like reference numerals have been used in FIGS. 21 and 22 to describe like components of overtube assemblies 42 and 321. The overtube assembly 321 has an end cap 322 secured to the distal end of overtube member 72 by any suitable means. At least one and as shown a single recess or vacuum cavity 323 is formed in the outer cylindrical wall of end cap 322. The recessed portion or vacuum cavity 323 extends circumferentially an angle of 360° about the longitudinal axis of overtube assembly 321, as shown in FIG. 21 and is formed by a semicircular-shaped wall 324. A plurality of circumferentially-disposed vacuum apertures 326 extend through wall or recess base 324. The vacuum apertures 326 are radially extending and circumferentially spaced around the longitudinal axis of overtube assembly 324 to fluidly connect circumferential recess 323 with pressure chamber 68 by means of central bore 223 to provide suction to the recess 323. Needle 96 is insertable into a selected portion of vacuum cavity 323 by means of a plurality of circumferentially-disposed bores or needle guides 330 which extend from the distal end of internal chamber through the proximal portion of recess wall 324.

In the operation of overtube assembly 321, a portion of the wall 232 to be treated is drawn into circumferential vacuum recess 323 as suction source 220 is activated. Such portion of wall 232 can substantially assume the shape of circumferential vacuum recess 323 so as to form at least a partial arcuate or circumferential protrusion, such as an arcuate protrusion of the type disclosed in U.S. Pat. No. 6,251,064. Needle guides 330 assist in guiding needle 96 into circumferential vacuum recess 323 as well as any protrusion formed therein. Although a single injection with a single needle 96 can be utilized for forming an implant in the portion of wall 232 drawn into vacuum cavity 323, in an alternate procedure a plurality of injections can be made by means of one or more needles 96.

Other circumferential recess geometries may also be used to provide various protrusion and implant shapes. For example, circumferential vacuum recesses similar to vacuum cavity 323 can be provided with any suitable profile such as any of the profiles or cross sections shown in FIGS. 18-20 in order to form circumferential protrusions of various desired shapes. One should appreciate that an arcuate vacuum recess can be provided that extends angularly about the longitudinal axis of the overtube assembly less than the entire circumference of the overtube assembly. For example, vacuum cavities can be provided that extend approximately 90° or 180° around an overtube assembly and be within the scope of the present invention.

Figure 23:
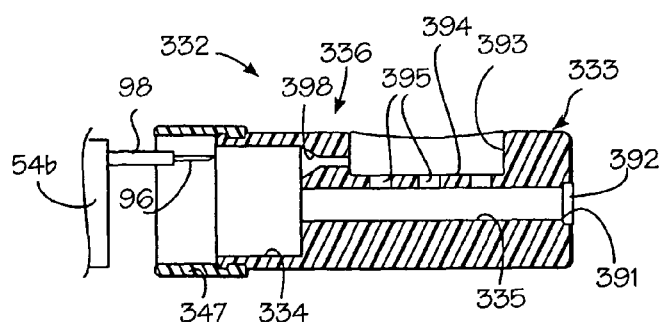
FIG. 23 is a cross-sectional view of a distal portion of yet another embodiment of the apparatus of the present invention.

In another embodiment of the present invention, as shown in FIG. 23, a short tubular assembly or overtip assembly 332 is used in combination with a conventional probe such as insertion tube 54. More specifically, second member or overtip assembly 332 is removably attached or mounted to distal end 54b of insertion tube 54. As such, overtip assembly 332 does not extend along the length of insertion tube 54 and, in use with the insertion tube, does not have a proximal portion accessible outside of body 238. In this regard, overtip assembly 332 has a length ranging from one to ten centimeters and preferably ranging from two to three centimeters. Overtip assembly includes a cylindrical body or end cap 333 made from plastic or any other suitable material. The end cap 333 has a diameter ranging from 0.5 to 2.5 centimeters and preferably ranging from 0.75 to 1.5 centimeters. A longitudinally-extending internal chamber 334 is provided at the proximal extremity of end cap 333 and a central bore 335 extends distally from chamber 334 to an opening 391 at the distal end or end cap 333. An optical window 392 similar to optical window 226 is sealably secured to end cap 333 at opening 391. At least one and as shown one vacuum recess or cavity 393 is provided in the outer cylindrical surface of end cap 333. The recess or vacuum cavity 393 is formed in part by a planar wall or base 394 and the cavity can have any suitable size and shape, including any of the shapes discussed above. A plurality of bores or apertures 395 extend through base 394 to fluidly connect the vacuum cavity 392 with central bore 335.

Means including a flexible tubular member or sleeve 397 is included in overtip assembly 332 for removably mounting end cap 333 to distal end 54b of insertion tube or probe 54. Sleeve 397 is made from any suitable material such as silicone, and is diametrically sized and has sufficient elasticity to extend over a portion of distal end 54 and secure thereto with a friction fit. The proximal end of end cap 333 generally abuts distal end 54b when overtip assembly 332 is so secured to the insertion tube 54. Sleeve 397 further serves as a seal and thus serves to provide a fluid-tight connection between insertion tube 54 and end cap 333. At least one longitudinally-extending bore or guide 398 extends from the distal end of internal chamber 334 to the proximal end of vacuum cavity 393 for permitting a needle 96 carried by insertion tube 54 to be removably inserted into the vacuum cavity 393.

In operation and use, overtip assembly 332 is mounted on distal end 54b of the insertion tube 54 prior to insertion of the tube 54 into the body 238. Suction is provided to internal chamber 334 and thus vacuum cavity 393 by means of insertion tube when it is desired to draw a portion of wall 232 into the cavity 393. Needle 96, slidably carried by insertion tube 54 and manipulable from outside of body 238, is inserted into the protrusion 230 formed in cavity 393 for injecting the implant-forming solution into protrusion 230 and thus wall 232 in the manner discussed above.

A further embodiment of an apparatus for forming implants in the wall of a cavity within a body of a mammal is shown in FIG. 24. The apparatus 337 therein includes insertion tube 54 and an overtip assembly 338 substantially similar to overtip assembly 332 described above. Like reference numerals have been used in FIG. 24 to identify like components of overtip assemblies 332 and 338. An end cap 339 substantially similar to end cap 333 and a flexible attachment sleeve 334 are included in the overtip assembly 338. End cap 339 has a central passageway or bore 340 extending longitudinally therethrough for permitting viewing with optical viewing device 43 forwardly of the overtip assembly 338. The relatively short length of overtip assembly 332 facilitates forward viewing by optical viewing device 48. Such forward viewing is further enhanced by forming central bore 340 with a relatively large diameter. Overtip assembly 338 does not include an optical window, such as optical window 392, on the distal end of central bore 340. As a result, bore 340 is not capable of providing negative pressure or suction to apertures 395 and the vacuum cavity 393 of end cap 339.

External means is included in apparatus 337 for providing suction to vacuum cavity 393 and includes an external suction tube 342 that extends externally alongside insertion tube 54. Suction tube 342 has a proximal end 342a connected to a conventional stop cock and fluid fitting assembly 343 for permitting the tube 342 to be connected in a fluid-tight manner to a suitable suction source such as suction source 220 described above. The suction tube has a distal end 342b that extends into end cap 339 and connects in a fluid-tight manner to apertures 395. External suction tube 342 can be secured alongside insertion tube 54 by any suitable means such as a small rubber sleeve 344 concentrically disposed about insertion tube 54 to hold suction tube 342 against its outer circumference.

Apparatus 337 further includes a multi-window overtube member 346 which slidably extends over overtip assembly 338 and insertion tube 54 for rotatable movement therewith. Overtube member 346 can be made from any suitable material such as plastic and is provided with a central passageway 347 for slidably and rotatably receiving the overtip assembly and insertion tube. The overtube member 346 has proximal and distal extremities 346a and 346b and has a length so that when the distal extremity 346b is inside the desired cavity of the body, such as the upper gastrointestinal tract, adjacent the targeted tissue, the proximal extremity 346a is outside of the body. A plurality and as shown a plurality of four circumferentially spaced-apart side openings 348 are formed in distal extremity 346b. A distal or end opening 349 is further provided in overtube member 346. Each of side openings 348 has a size and shape which approximates the size and shape of the opening of vacuum cavity 393 and is longitudinally positioned on the overtube member 346 so that when the overtip assembly 338 abuts the end of the overtube member 346, one of the openings 348 can be selectively registered with the vacuum cavity 393. End opening 349 preferably has a size and shape approximating the size of central bore 340 of the overtip assembly 339 for permitting forward viewing through the overtube member 346. A flange member or handle 350 is formed on proximal extremity 346a of overtube member 346 for facilitating rotation of the overtube member about insertion tube 54 and overtip assembly 338.

In operation and use, overtube member 346 serves to facilitate rotation of overtip assembly 338 and insertion tube 54 within the body cavity, particularly where the overtube member is snugly disposed within such body cavity. Where, for example, a probe is so snugly disposed in a body cavity, apposition of soft tissue to the probe can occur and thus hinder rotation of the probe within the cavity. As a result, the ability of the operating physician to desirably position the probe within the cavity may be limited. Overtube member 346, which has multiple side openings or windows 348, overcomes this disadvantage when used within an esophagus 240 by allowing the operating physician to adjust the position of the overtube member 346 by rotating the overtube member 346 within esophagus 240 or other body passageway once and then treat several areas therein by rotating insertion member 54 and overtip assembly 338 within the overtube member to one or more of the several positions in which vacuum cavity 393 of the overtip assembly registers with a side window 348 of the overtube member. Apposition of soft tissue to apparatus 337 is reduced and/or eliminated because overtube member 346 is not repeatedly rotated within the esophagus.

Overtip assembly 338 is provided with only a single vacuum cavity 393. This advantageously enhances the suction forces exerted on the protrusion formed in the vacuum cavity 393, in contrast to an overtube assembly or overtip assembly in which only one of multiple vacuum cavities is engaging wall 232 and thus the remainder of the vacuum cavities are open within the gastrointestinal tract thereby reducing the vacuum force capable of being supplied by the common suction source to the selected vacuum cavity. A dedicated vacuum supply is provided to single cavity 393 by means of external suction tube 342. As discussed above, vacuum cavity 393 is registerable with the desired side opening 348 in overtube member 346 during operation.

Forward visualization is optimized by means of foreshortened overtip assembly 338, large diametered central bore 340 in the overtip assembly and the unobstructed openings at the distal ends of the overtip assembly 338 and the overtube member 346.

In other embodiments, apparatus can be provided having means for urging the vacuum recess against the targeted wall portion for enhancing formation of implants in the wall. For example, apparatus 351 shown in FIG. 25 has urging means in the form of a balloon. Apparatus 351 has an overtip assembly 352 substantially similar to overtip assembly 332. Like reference numerals have been used in FIG. 25 to identify like components of overtip assemblies 352 and 332. The overtip assembly 352 is mounted on distal end 54b of insertion tube 54 by any suitable means such as flexible sleeve 397.

An inflatable balloon 353 is carried within a recess 354 provided on end cap 339 generally opposite vacuum cavity 393. An externally mounted air feeding or air supply tube 355 is provided to inflate balloon 353. Supply tube 355 has a proximal end 355a connected to a conventional stop cock and fluid fitting assembly 399 for permitting the tube 355 to be connected in a fluid-tight manner to a suitable fluid inflation supply (not shown). The supply tube has a distal end 355 that extends into end cap 339 and connects in a fluid-tight manner to balloon 353. Air supply tube 355 may be mounted externally on insertion tube 54 in the same manner as suction tube 342 discussed above, for example by means of rubber sleeve 344. Alternatively, an air or inflation fluid tube internal of insertion tube 54 can be provided for inflating balloon 353.

In operation and use, balloon 353 is used to bias or urge insertion tube 54 and overtip assembly 338 against the portion of wall 232 to be captured within cavity 393 and implanted. Balloon 353 facilitates placement of vacuum cavity 393 against wall 232 and the creation of suction within the vacuum cavity by pressing end cap 339 against the opposite portion of the wall of the esophagus or other body passageway being implanted. Balloon 353 can be used independent of suction source 220 or used in conjunction with suction source 220 to urge the targeted portion of the wall of the esophagus or other body passageway into implantation cavity 393 for injection by needle 96. It should also be appreciated that a balloon such as balloon 353 can be provided in any of the embodiments of the invention discussed above.

When balloon 352 is used in conjunction with suction source 220, an externally mounted suction tube 342 and air supply tube 355 may be provided. In one embodiment, an externally mounted dual lumen tube may be provided in which one lumen of the tube is fluidly connected to vacuum cavity 393 for providing suction thereto and the other lumen of the tube is fluidly connected to balloon 355 for supplying air thereto.

Figure 26:
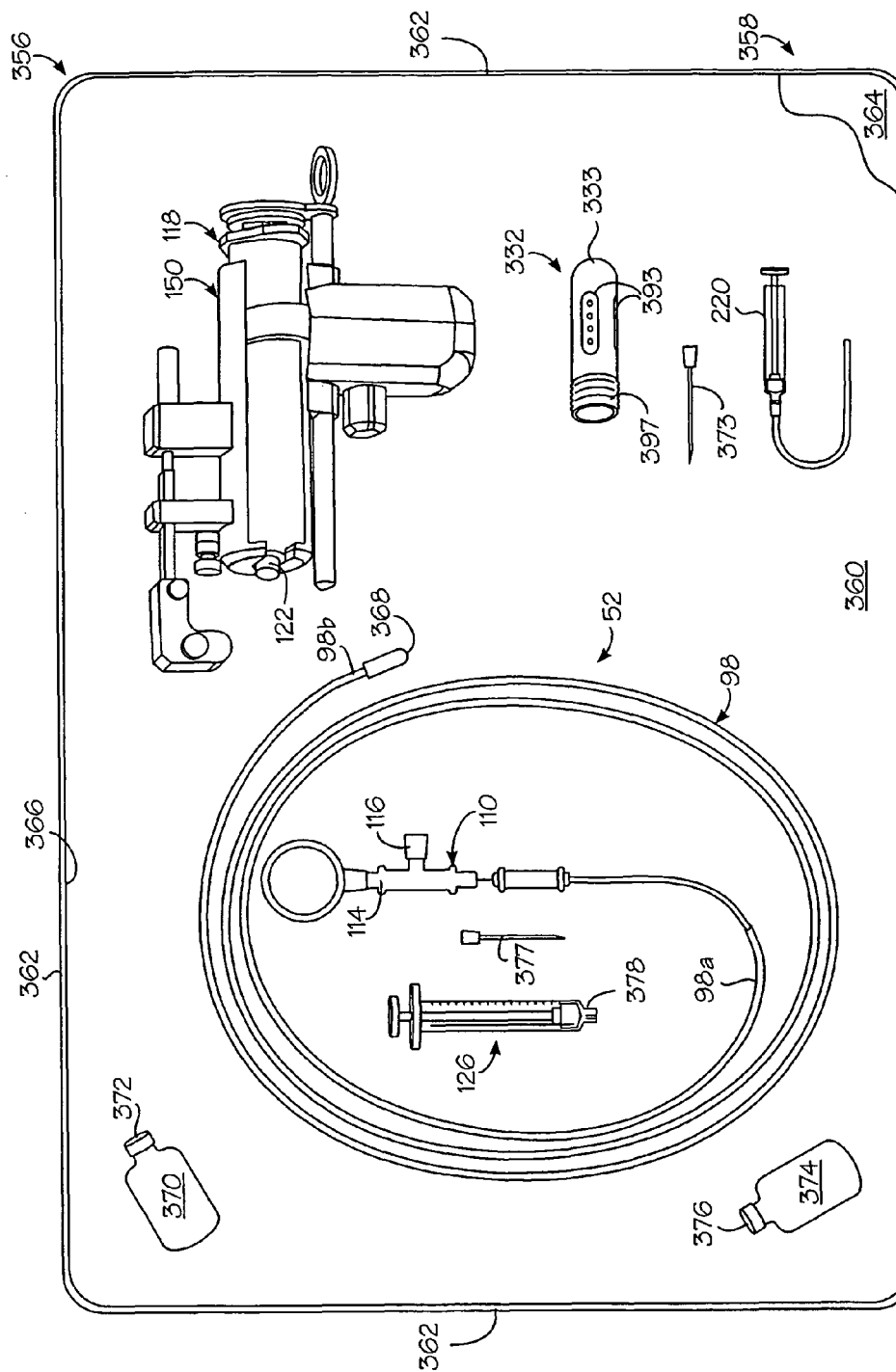
FIG. 26 is a plan view of a kit, somewhat schematic and partially cut away, for treating a portion of a wall forming a cavity in a body in accordance with the present invention.

A kit 356 for use in forming a protrusion in a wall and treating the wall forming the upper portion of a gastrointestinal tract in a human body in accordance with the method of the present invention is shown schematically in FIG. 26. Kit 356 includes a package 358 made from any suitable material such as cardboard or plastic for carrying the contents thereof. An exemplary package 358, shown in FIG. 26, is a box formed from a bottom wall 360, four side walls 362 and a top wall 364. A portion of top wall 364 is cut away in FIG. 26 to reveal an internal space 366 formed by walls 360, 362 and 364. The contents of receptacle or package 358 are disposed in internal space 366.

Needle assembly 52 is carried by package 358 within internal space 366. As discussed above, needle assembly 52 includes a needle 96 within a sleeve 98 and a fluid connector 110. A cap 368 is removably attached to distal end portion 98b of the sleeve 98 for protecting users against undesirable punctures by needle distal end portion 96b during storage and setup. Luer fitting portions 114 and 116 of fluid connector 110 are shown as being capped in FIG. 26. Kit 356 further includes reservoir or syringe 118 and a container or vial 370 of any suitable implant forming solution. In one preferred embodiment, the implant forming material is the nonaqueous implant-forming solution referred to above. Vial 370 has a needle-penetrable cap 372 and Luer fitting portion 122 of syringe 118 is attached to a standard hypodermic needle 373, optionally included within kit 356, that is removably coupled to cap 372 by penetrating the cap 372 for loading the syringe 118. As discussed above, Luer fitting portion 122 of the syringe 118 is also removably coupled to fluid connector 110 of needle assembly 52.

A tubular assembly, such as overtip assembly 332, is included within kit 356 for forming protrusions in gastrointestinal walls as discussed above. Although overtip assembly 332 is shown in FIG. 26, kit 356 may include longer overtube assemblies, such as overtube assembly 42 shown in FIGS. 1-3, instead of or in addition to overtip assembly 332. Kit 356 can also optionally include a suitable suction source 220, shown in FIG. 26 as being a syringe, for producing a negative pressure within the pressure chamber and vacuum recesses 393 of end cap 333.

A delivery mechanism such as gun 150 for supplying a plurality of discrete preselected amounts of the nonaqueous solution from syringe 118 can optionally be included within kit 356. Syringe 118 is shown in FIG. 26 as being mounted within gun 150. Additional optional components of kit 356 include a second reservoir, such as syringe 126, and a container of a biocompatible solvent such as DMSO in the form of vial 374. Vial 374 includes a needle-penetrable cap 376 and syringe 126 has a Luer fitting portion 378 that is attachable to a standard hypodermic needle 377, optionally included in kit 356, that is removably coupled to cap 376 of the vial 374. Kit 356 can optionally further include a plurality of stopcocks, such as stopcocks 132, 134, 136 and not shown in FIG. 26, for forming a manifold assembly 130 suitable for selectively directing the flow of liquid through needle assembly 52 in the manner discussed above. A third reservoir or syringe (not shown) and/or a vial of aqueous solution such as saline solution (not shown) can also be optionally included in kit 356.

Kit 356 can be used in any of the procedures described above or in any other procedure for treating wall 232 in the upper gastrointestinal tract. Needle assembly 52 of the kit 356 is preferably used with a probe device such as probe 44 described above with reference to FIGS. 1-3, 6 and 7. In this regard, needle assembly 52 is diametrically sized for introduction into the gastrointestinal tract through probe 44 and, more particularly, through working channel 88 of probe insertion tube 54. Syringe 118 is loaded with the nonaqueous solution from vial 331 by any suitable means such as coupling Luer fitting portion 122 of the syringe 118 to hypodermic needle 373 for penetrating cap 332 of the vial 330. When filled, syringe 118 is attached to fluid connector 110 in a manner discussed above. Probe 44 is introduced into esophagus 240 until distal extremity 54b of insertion tube 54 is in the vicinity of the treatment area. Thereafter, distal end portions 96b and 98b of needle assembly 22 are advanced through insertion tube 54 until such distal end portions of needle 96 and sleeve 98 are in the vicinity of insertion tube distal extremity 54b.

When gun 150 is so used, syringe 118 is mounted within the gun in a manner discussed above. In addition, optional syringe 126 can be used for supplying a suitable biocompatible solvent such as DMSO through needle assembly 52 during the procedure. The syringe 126 is filled by removably coupling Luer fitting portion 378 thereof to hypodermic needle 377 for penetrating cap 376 of vial 374. Thereafter, the syringe 126 is coupled to fluid connector 110 in a manner discussed above. In addition, optional saline solution syringe 128 can be coupled to fluid connector 110 in a manner discussed above for use during the procedure.

Overtip assembly 332 can be mounted on distal end 54b of insertion tube 54 for facilitating the creation of implants in the targeted wall of the body 238.

Kit 356 can be used for treating tracheo-esophageal fistulas, veins and arteries and gastric ulcers in the manner described above. Kit 356 can also be used in any other procedure within the upper gastrointestinal tract or other suitable cavity within a body where it is desired to form implants in the wall of the gastrointestinal tract or such cavity.

Figure 27:
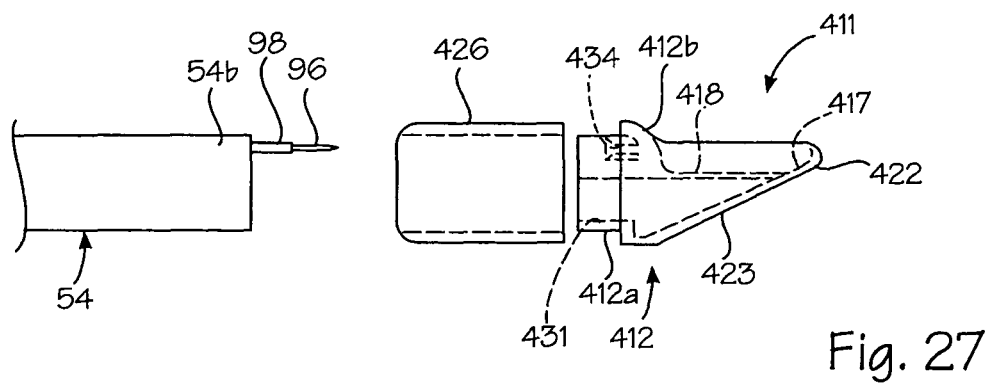
FIG. 27 is an exploded side elevational view of the distal portion of a further embodiment of the apparatus of the present invention.
Figure 28:
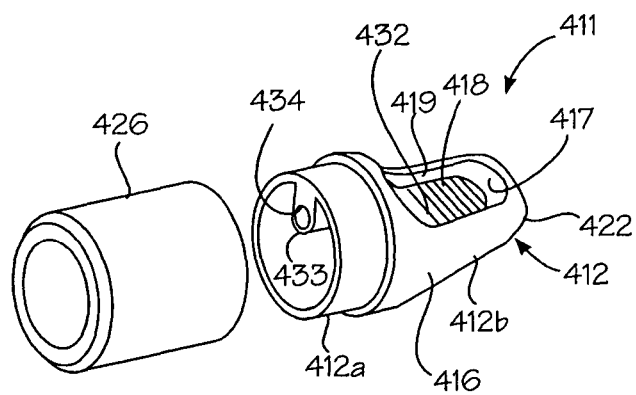
FIG. 28 is an exploded perspective view of a portion of the apparatus of FIG. 27.
Figure 29:
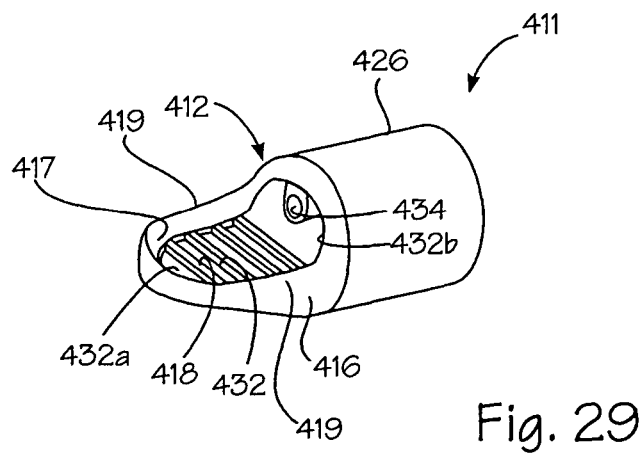
FIG. 29 is an assembled perspective view of the portion of the apparatus shown in FIG. 28.

A further embodiment of the treatment device of the present invention is shown in FIGS. 27-29. The portion of the treatment device shown therein includes an additional member or short overtip assembly 411 for use with insertion probe 54. Overtip assembly 411 is similar to overtip assembly 332 described above and includes an end piece or end cap 412 made from any suitable hard plastic such as PMP or acrylic. The end piece 412 is preferably optically clear. End piece 412 has proximal and distal extremities 412a and 412b centered on a longitudinal axis and has a length ranging from one to ten centimeters and preferably ranging from one to three centimeters.

Distal extremity 412b of the end piece is formed from an outer cylindrical wall 416. At least one recessed portion or recess 417 is provided in overtip assembly 411 and, as shown in FIGS. 27-29, a single recess 417 is formed in outer cylindrical wall 416 of the distal extremity 412b. The recess 417 is cup-shaped and formed from a base wall or base 418 and a peripheral wall or rim 419. End piece 412 has a blunt nose 422 formed by the distal end of peripheral wall 419. A planar wall in the form of optics window 423 extends at an oblique angle to the longitudinal axis of the end piece from blunt nose 422. Window 423 is disposed substantially opposite recess 417 and extends below the recess 417.

Means is included in overtip assembly 411 for removably mounting end piece 412 to the distal end of a probe such as insertion tube 54. Such means includes a sleeve 426 substantially similar to sleeve 397 and made from any suitable material such as silicone. The tubular sleeve 426 has an internal diameter that is sized to snugly receive the distal end of insertion tube 54. Proximal extremity 412a of end piece 412 is annular in conformation and diametrically sized relative to sleeve 426 to snugly receive the distal end of sleeve 426 thereover. Sleeve 426 thus serves to secure end piece 412 to insertion tube 54 as well as provide a fluid tight seal between the end piece and the insertion tube.

An internal chamber or passageway 431 is provided inside the hollow end piece 412. A plurality of passageways or openings 432 extend through the base 418 of recess 417 for providing fluid communication between internal chamber 431 and the recess 417. Although openings 432 can be of any suitable size and shape, the openings 432 are shown as including a plurality of slots 432a extending across base 418 substantially perpendicular to the longitudinal axis of overtip assembly 411 and a large opening 432b formed below rim 419 at the proximal end of the recess 417.

End piece 412 is provided with a needle guide 433 for directing a needle slidably carried within insertion tube 54, such as needle 96 shown in FIG. 27, into the proximal end of recess 417. The needle guide depends from the annular wall of end piece proximal extremity 412a and extends from the opening at the proximal end of internal chamber 431 into recess 417 by means of the large proximal opening 432b. Needle guide 433 has a bore 434 which extends from the proximal end of end piece 412 into the recess 417. The proximal end of the bore 434 is flared for facilitating the capture of needle 96 by guide 433.

In operation and use, overtip assembly 411 can be removably mounted on the distal end 54b of insertion tube 54 by means of elastic sleeve 426. Distal extremity 54b of the insertion tube is received by the sleeve 426 and generally abuts proximal extremity 412a of end piece 412. The overtip assembly 411 and insertion tube 84 are introduced into the appropriate cavity of the body, such as through the mouth into the esophagus, in the manner discussed above.

Overtip assembly 411 is advantageously sized and constructed so as to facilitate its advancement into and through the esophagus and the treatment of the desired portion of the esophageal wall 232. The relatively short length of end piece 412 permits the overtip assembly 411 to be easily navigated through the entrance of the esophagus, particularly in the vicinity of the vocal chords. The optically clear material of the end piece contributes to the illumination, by light guides 82, and resulting clarity of the wall 232. Forward viewing with minimal distortion is permitted by planar window 423. The relatively short length of end piece 412 as well as the relatively large transverse dimension of internal chamber 431 provide optical viewing device 48 with a relatively large field of view.

After proper placement of the overtip assembly 411 within the esophagus, suction from source 220 is provided to recess 417 by means of slots 432a and proximal opening 432b. The desired portion of wall 232 to be treated is pulled into recess 417 by such suction, with slots 432a pulling the tissue against the base of the recess 417 and proximal opening 432b pulling the tissue up against the distal end of needle guide 433 at the proximal end of recess 417. Thereafter, needle 96 is advanced from insertion tube 54 through needle guide 433 into the protrusion 230 (not shown) formed within recess 417 so as to permit one or more implants to be formed in the protrusion in the manner discussed above. The taut retention of the protrusion in the recess 417 by openings 432 facilitates the repeatable formation of similar implants. The positioning of insertion tube distal extremity 54b relative to end piece 412 and the relatively large transverse dimension of internal chamber 431 permit the optical viewing device 48 to easily view needle 96 being introduced into recess 417 and the protrusion 230 to be formed therein.

As can be seen from the foregoing, a minimally invasive apparatus has been provided for injecting a material into a portion of a wall forming a cavity in a body, such as the gastrointestinal tract, to form one or more implants of a substantially consistent size in the wall. A recess in a probe is utilized to shape the portion of the wall into a protrusion into which the material is injected. The probe guides and positions an injection needle into the protrusion. Consistently sized multiple implants may be formed in a portion of the wall of the cavity. The probe inhibits the injection need from being pushed through the wall of the cavity. The apparatus and procedure can be utilized for treating gastroesophageal reflux disease.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A kit for use with an elongate probe member having proximal and distal extremities and an end face provided with a diameter to treat a wall forming the upper portion of a gastrointestinal tract in a body of a mammal comprising a package, a tubular needle adapted for slidable disposition in the elongate probe member carried within the package and having proximal and distal end portions, an end piece adapted to mount to the distal extremity of the elongate probe member carried within the package, the end piece having a diameter at least as large as the diameter of the end face so as to overlie the end face and an outer cylindrical surface and being provided with at least one recess opening onto the outer cylindrical surface and an internal passageway communicating with the recess, and a container of an implant-forming material carried within the package whereby the end piece is mounted on the distal extremity of the elongate probe member and introduced into the upper portion of the gastrointestinal tract where a portion of the wall is drawn into the recess and whereby the tubular needle is extended through the internal passageway into the portion of the wall in the recess and material is loaded into the tubular needle and injected into the portion of the wall to form an implant in the wall.

2. The kit of claim 1 wherein the implant-forming material includes a solution having a biocompatible polymer and a biocompatible solvent.

3. The kit of claim 2 wherein the solution of the biocompatible polymer and the biocompatible solvent has a composition having from about 2.5 to about 8.0 weight percent of a biocompatible polymer, from about 10 to about 40 weight percent of a water insoluble biocompatible contrast agent and from about 52 to about 87.5 weight percent of a biocompatible solvent.

4. The kit of claim 1 wherein the implant-forming material includes a biocompatible prepolymer whereby the prepolymer polymerizes in situ to form the implant in the wall.

5. The kit of claim 1 wherein the container further includes a contrast agent for facilitating visualization of the implant in the wall.

6. A kit for use with an elongate probe member having proximal and distal extremities and an end face provided with a diameter to treat a wall forming the upper portion of a gastrointestinal tract in a body of a mammal comprising a package, a tubular needle adapted for slidable disposition in the elongate probe member carried within the package and having proximal and distal end portions, an end piece adapted to mount to the distal extremity of the elongate probe member carried within the package, the end piece having a diameter at least as large as the diameter of the end face so as to overlie the end face and an outer cylindrical surface and being provided with at least one recess opening onto the outer cylindrical surface and an internal passageway communicating with the recess, a syringe removably couplable to the proximal end portion of the tubular needle carried within the package and a container of a solution for forming a nonbiodegradable solid in the wall carried within the package whereby the end piece is mounted on the distal extremity of the elongate probe member and introduced into the upper portion of the gastrointestinal tract where a portion of the wall is drawn into the recess and whereby the tubular needle is extended through the internal passageway into the portion of the wall in the recess and solution is loaded by the syringe into the tubular needle and injected into the portion of the wall to form a nonbiodegradable solid in the wall.

7. The kit of claim 6 wherein the tubular needle has a length so that when the distal end portion is in the vicinity of the lower esophageal sphincter the proximal end portion is outside of the body.

8. The kit of claim 6 wherein the solution includes a biocompatible polymer and a biocompatible solvent.

9. The kit of claim 6 further comprising an additional container of a biocompatible solvent carried within the package.

10. The kit of claim 6 further comprising a delivery mechanism for supplying a plurality of discrete preselected amounts of the solution from the syringe to the tubular needle for introduction into the wall.

11. The kit of claim 6 wherein the solution includes a biocompatible prepolymer whereby the prepolymer polymerizes in situ to form the nonbiodegradable solid in the wall.

12. The kit of claim 11 wherein the solution includes a biocompatible solvent.

13. The kit of claim 6 wherein the solution is a nonaqueous solution.

14. The kit of claim 6 wherein the solution includes a contrast agent for facilitating visualization of the nonbiodegradable solid in the wall.

15. The kit of claim 6 wherein the recess extends circumferentially around the outer cylindrical surface.

16. The kit of claim 6 wherein the end piece is provided with a plurality of circumferentially spaced-apart recesses in the outer cylindrical surface.

17. A kit for use with an elongate probe member having proximal and distal extremities to treat a wall forming the upper portion of a gastrointestinal tract in a body of a mammal comprising a package, a tubular needle adapted for slidable disposition in the elongate probe member carried within the package and having proximal and distal end portions, an end piece adapted to mount to the distal extremity of the elongate probe member carried within the package, the end piece having an outer cylindrical surface and being provided with a recess extending circumferentially around the entire outer cylindrical surface and a container of an implant-forming material carried within the package whereby the end piece is mounted on the distal extremity of the elongate probe member and introduced into the upper portion of the gastrointestinal tract where a portion of the wall is drawn into the recess and whereby the tubular needle is extended into the portion of the wall in the recess and material is loaded into the tubular needle and injected into the portion of the wall to form an implant in the wall.

18. The kit of claim 17 wherein the implant-forming material includes a solution having a biocompatible polymer and a biocompatible solvent.

19. The kit of claim 17 wherein the implant-forming material includes a biocompatible prepolymer whereby the prepolymer polymerizes in situ to form the implant in the wall.

20. The kit of claim 17 wherein the container further includes a contrast agent for facilitating visualization of the implant in the wall.

21. A kit for use with an elongate probe member having proximal and distal extremities and an end face provided with a diameter to treat a wall forming the upper portion of a gastrointestinal tract in a body of a mammal comprising a package, a tubular needle adapted for slidable disposition in the elongate probe member carried within the package and having proximal and distal end portions, an end piece adapted to mount to the distal extremity of the elongate probe member carried within the package, the end piece having a diameter approximating the diameter of the end face so as to overlie the entire end face and an outer cylindrical surface and being provided with at least one recess opening onto the outer cylindrical surface and an internal passageway communicating with the recess, and implant-forming material carried within the package whereby the end piece is mounted on the distal extremity of the elongate probe member and introduced into the upper portion of the gastrointestinal tract where a portion of the wall is drawn into the recess and whereby the tubular needle is extended through the internal passageway into the portion of the wall in the recess and material is loaded into the tubular needle and injected into the portion of the wall to form an implant in the wall.

22. The kit of claim 21 wherein the implant-forming material includes a solution having a biocompatible polymer and a biocompatible solvent.

23. The kit of claim 22 wherein the solution of the biocompatible polymer and the biocompatible solvent has a composition having from about 2.5 to about 8.0 weight percent of a biocompatible polymer, from about 10 to about 40 weight percent of a water insoluble biocompatible contrast agent and from about 52 to about 87.5 weight percent of a biocompatible solvent.

24. The kit of claim 21 wherein the implant-forming material includes a biocompatible prepolymer whereby the prepolymer polymerizes in situ to form the implant in the wall.

25. The kit of claim 21 wherein the implant-forming material includes a contrast agent for facilitating visualization of the implant in the wall.

26. A kit for use with an elongate probe member having proximal and distal extremities and an end face provided with a diameter to treat a wall forming the upper portion of a gastrointestinal tract in a body of a mammal comprising a package, a tubular needle adapted for slidable disposition in the elongate probe member carried within the package and having proximal and distal end portions, an end piece adapted to mount to the distal extremity of the elongate probe member carried within the package, the end piece having a diameter approximating the diameter of the end face so as to overlie the entire end face and an outer cylindrical surface and being provided with at least one recess opening onto the outer cylindrical surface and an internal passageway communicating with the recess whereby the end piece is mounted on the distal extremity of the elongate probe member and introduced into the upper portion of the gastrointestinal tract where a portion of the wall is drawn into the recess and whereby the tubular needle is extended through the internal passageway into the portion of the wall in the recess.

27. The kit of claim 26 wherein the recess extends circumferentially around the outer cylindrical surface.

28. The kit of claim 26 wherein the end piece is provided with a plurality of circumferentially spaced-apart recesses in the outer cylindrical surface.

* * * * *